United States Patent
Bae et al.

(10) Patent No.: US 10,164,198 B2
(45) Date of Patent: Dec. 25, 2018

(54) ORGANOMETALLIC COMPOUND, COMPOSITION CONTAINING ORGANOMETALLIC COMPOUND, AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Hyejin Bae, Suwon-si (KR); Wook Kim, Suwon-si (KR); Changho Noh, Suwon-si (KR); Rupasree Ragini Das, Suwon-si (KR); Virendra Kumar Rai, Hwaseong-si (KR); Miyoung Chae, Suwon-si (KR); Dmitry Kravchuk, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 547 days.

(21) Appl. No.: 14/810,863

(22) Filed: Jul. 28, 2015

(65) Prior Publication Data
US 2016/0233440 A1    Aug. 11, 2016

(30) Foreign Application Priority Data

Feb. 5, 2015 (KR) .................. 10-2015-0018137

(51) Int. Cl.
| | | |
|---|---|---|
| H01L 51/54 | (2006.01) | |
| C09K 11/06 | (2006.01) | |
| H01L 51/00 | (2006.01) | |
| C07F 15/00 | (2006.01) | |
| C09K 11/02 | (2006.01) | |
| H01L 51/50 | (2006.01) | |

(52) U.S. Cl.
CPC ...... *H01L 51/0085* (2013.01); *C07F 15/0033* (2013.01); *C09K 11/025* (2013.01); *C09K 11/06* (2013.01); *C09K 2211/1011* (2013.01); *C09K 2211/1044* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 7,585,573 B2 | 9/2009 | Lee et al. | |
| 8,142,909 B2 | 3/2012 | Beers et al. | |
| 8,148,891 B2 | 4/2012 | Tung et al. | |
| 2008/0233433 A1* | 9/2008 | Igarashi et al. ........ | C09K 11/06 428/704 |
| 2013/0032766 A1 | 2/2013 | Molt et al. | |
| 2013/0168656 A1 | 7/2013 | Tsai et al. | |
| 2013/0293094 A1 | 11/2013 | Dyatkin et al. | |
| 2014/0054563 A1 | 2/2014 | Xia et al. | |
| 2014/0073076 A1 | 3/2014 | D'Andrade et al. | |
| 2018/0019414 A1 | 1/2018 | Lin et al. | |

FOREIGN PATENT DOCUMENTS

| | | |
|---|---|---|
| KR | 1020140026282 A | 3/2014 |
| KR | 10-2014-0041551 A | 4/2014 |
| WO | 0215645 A1 | 2/2002 |
| WO | 2005019373 A2 | 3/2005 |
| WO | 2006009024 A1 | 1/2006 |
| WO | 2012170463 A1 | 12/2012 |
| WO | 2012170571 A1 | 12/2012 |
| WO | 2013061850 A1 | 5/2013 |

OTHER PUBLICATIONS

Ruben Seifert, et al., "Chemical degradation mechanisms of highly efficient blue phosphorescent emitters used for organic light emitting diodes", Organic Electronics 14 (2013) 115-123.

\* cited by examiner

*Primary Examiner* — Marie R. Yamnitzky
(74) *Attorney, Agent, or Firm* — Cantor Colburn LLP

(57) ABSTRACT

An organometallic compound represented by Formula 1:

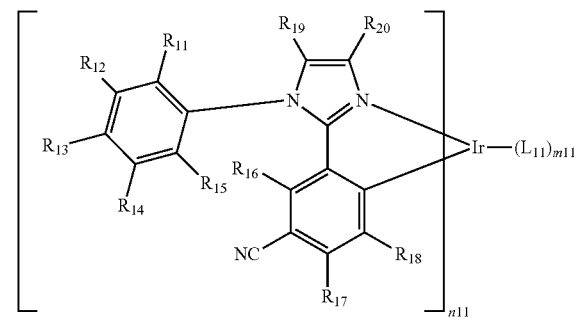

wherein in Formula 1, $R_{11}$ to $R_{20}$, $L_{11}$, $m_{11}$, and $n_{11}$ are the same as described in the specification.

19 Claims, 5 Drawing Sheets

ORGANOMETALLIC COMPOUND, COMPOSITION CONTAINING ORGANOMETALLIC COMPOUND, AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0018137, filed on Feb. 5, 2015, in the Korean Intellectual Property Office, the disclosure of which is incorporated herein in its entirety by reference.

BACKGROUND

1. Field

The present disclosure relates to an organometallic compound, a composition containing an organometallic compound, and an organic light-emitting device including the same.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons. These excitons change from an excited state to a ground state to thereby generate light.

Various types of organic light emitting devices are known. However, there still remains a need in OLEDs having low driving voltage, high efficiency, high brightness, and long lifespan.

SUMMARY

Provided are an organometallic cyclic compound and an organic light-emitting device including the same.

Additional aspects will be set forth in part in the description which follows and, in part, will be apparent from the description, or may be learned by practice of the presented exemplary embodiments.

According to an aspect of an exemplary embodiment, an organometallic compound is represented by Formula 1:

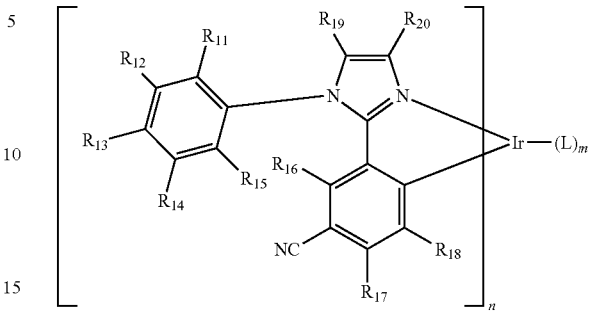

Formula 1 wherein in Formula 1, $R_{11}$, $R_{12}$, and $R_{14}$ to $R_{18}$ are each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{13}$ is selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ linear alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{19}$ and $R_{20}$ are each independently selected from a hydrogen, a deuterium, a $C_1$-$C_{10}$ alkyl group, and a $C_1$-$C_{10}$ alkyl group substituted with a deuterium;

at least one of $R_{11}$ to $R_{20}$ is a deuterium-containing substituent;

n11 is selected from 1, 2, and 3;

$L_{11}$ is selected from a monodentate ligand and a bidentate ligand; and m11 is selected from 0, 1, 2, 3, and 4.

According to one or more exemplary embodiments, a composition containing an organometallic compound, includes:

a first organometallic compound represented by Formula 1 and a second organometallic compound represented by Formula 2:

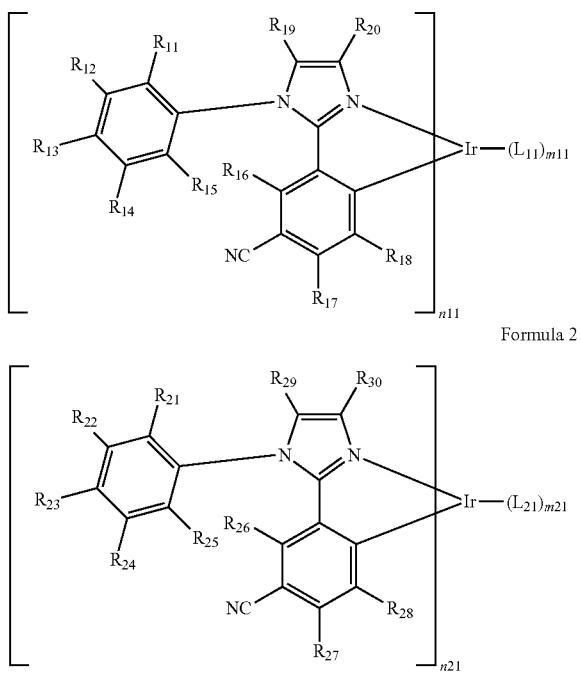

Formula 1

Formula 2 wherein in Formulae 1 and 2, $R_{11}$, $R_{12}$, and $R_{14}$ to $R_{18}$ are each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{13}$ is selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ linear alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{19}$ and $R_{20}$ are each independently selected from a hydrogen, a deuterium, a $C_1$-$C_{10}$ alkyl group, and a $C_1$-$C_{10}$ alkyl group substituted with a deuterium;

at least one of $R_{11}$ to $R_{20}$ is a deuterium-containing substituent;

$R_{21}$, $R_{22}$, and $R_{24}$ to $R_{28}$ are each independently selected from a hydrogen, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{23}$ is selected from a hydrogen, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ linear alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{29}$ and $R_{30}$ are each independently selected from a hydrogen and a $C_1$-$C_{10}$ alkyl group;

$R_{21}$ to $R_{30}$ are each a substituent comprising no deuterium;

n11 and n21 are each independently selected from 1, 2, and 3;

$L_{11}$ and $L_{21}$ are each independently selected from a monodentate ligand and a bidentate ligand; and m11 and m21 are each independently selected from 0, 1, 2, 3, and 4.

According to an aspect of another exemplary embodiment, an organic light-emitting device includes:
a first electrode;
a second electrode; and
an organic layer disposed between the first electrode and the second electrode,
wherein the organic layer includes an emission layer and at least one organometallic compound represented by Formula 1.

The emission layer may include the organometallic compound, the emission layer may further include a host, and the organometallic compound included in the emission layer may serve as a dopant.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
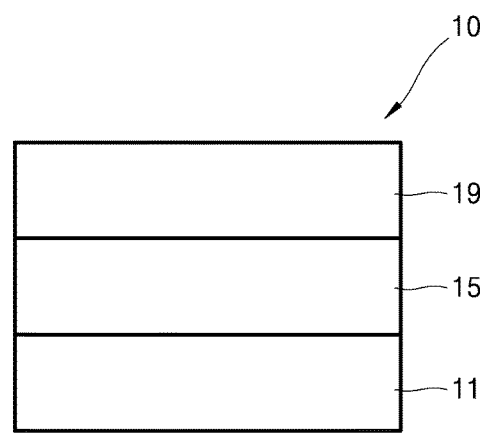
FIG. 1 is a schematic cross-sectional view illustrating an organic light-emitting device according to an embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

An organometallic compound is represented by Formula 1:

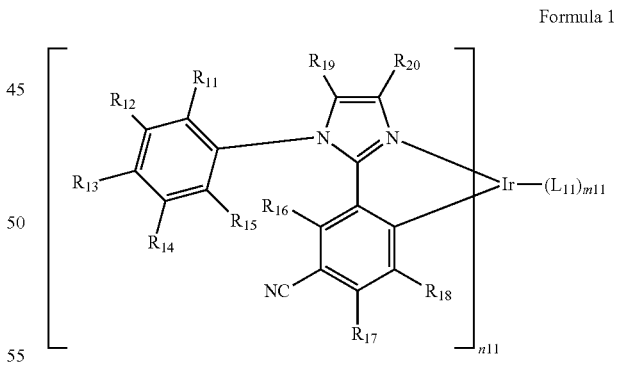

Formula 1 wherein in Formula 1, $R_{11}$, $R_{12}$, and $R_{14}$ to $R_{18}$ may be each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group.

In some embodiments, in Formula 1, $R_{11}$, $R_{12}$, and $R_{14}$ to $R_{18}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a substituted or unsubstituted $C_1$-$C_{10}$ alkyl group, but embodiments are not limited thereto.

In some embodiments, in Formula 1, $R_{11}$, $R_{12}$, and $R_{14}$ to $R_{18}$ may be each independently selected from a hydrogen, a deuterium, —F, —Cl, —Br, —I, a cyano group, and a $C_1$-$C_{10}$ alkyl group; and a $C_1$-$C_{10}$ alkyl group substituted with at least one selected from a deuterium, —F, —Cl, —Br, —I, and a cyano group, but embodiments are not limited thereto.

In some embodiments, in Formula 1, $R_{11}$, $R_{12}$, and $R_{14}$ to $R_{18}$ may be each independently selected from a hydrogen, a deuterium, —F, —Cl, —Br, —I, a cyano group, and a $C_1$-$C_{10}$ alkyl group; and a $C_1$-$C_{10}$ alkyl group substituted with a deuterium, but embodiments are not limited thereto.

In some embodiments, in Formula 1, $R_{11}$, $R_{12}$, and $R_{14}$ to $R_{18}$ may be each independently selected from a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group; and a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with a deuterium, but embodiments are not limited thereto.

In some embodiments, in Formula 1, $R_{11}$, $R_{12}$, and $R_{14}$ to $R_{15}$ may be each independently selected from a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, and a tert-butyl group; and a methyl group, an ethyl group, an n-propyl group, an iso-propyl group, an n-butyl group, a sec-butyl group, an iso-butyl group, and a tert-butyl group, each substituted with a deuterium, but embodiments are not limited thereto.

In some embodiments, in Formula 1, $R_{11}$, $R_{15}$, and $R_{17}$ may be each independently selected from a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, and a tert-butyl group; and a methyl group, an ethyl group, an n-propyl group, an iso-propyl group, an n-butyl group, a sec-butyl group, an iso-butyl group, and a tert-butyl group, each substituted with a deuterium, but embodiments are not limited thereto.

In some embodiments, in Formula 1, $R_{11}$ or $R_{15}$ may be each independently selected from a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, and a tert-butyl group; and a methyl group, an ethyl group, an n-propyl group, an iso-propyl group, an n-butyl group, a sec-butyl group, an iso-butyl group, and a tert-butyl group, each substituted with a deuterium, but embodiments are not limited thereto.

In some embodiments, in Formula 1, $R_{11}$ and $R_{15}$ may be each independently selected from a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, and a tert-butyl group; and a methyl group, an ethyl group, an n-propyl group, an iso-propyl group, an n-butyl group, a sec-butyl group, an iso-butyl group, and a tert-butyl group, each substituted with a deuterium, but embodiments are not limited thereto.

In some embodiments, in Formula 1, $R_{13}$ may be selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ linear alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group.

In some embodiments, in Formula 1, $R_{13}$ may be selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, and a substituted or unsubstituted $C_1$-$C_{10}$ linear alkyl group, but embodiments are not limited thereto.

In some embodiments, in Formula 1, $R_{13}$ may be selected from a hydrogen, a deuterium, —F, —Cl, —Br, —I, a cyano group, a $C_1$-$C_{10}$ linear alkyl group; and a $C_1$-$C_{10}$ linear alkyl group substituted with at least one selected from a deuterium, —F, —Cl, —Br, —I, and a cyano group, but embodiments are not limited thereto.

In some embodiments, in Formula 1, $R_{13}$ may be selected from a hydrogen, a deuterium, —F, —Cl, —Br, —I, a cyano group, and a $C_1$-$C_{10}$ linear alkyl group; and a $C_1$-$C_{10}$ linear alkyl group substituted with a deuterium, but embodiments are not limited thereto.

In some embodiments, in Formula 1, $R_{13}$ may be selected from a hydrogen, a deuterium, —F, —Cl, —Br, —I, a cyano group, a methyl group, an ethyl group, an n-propyl group, an n-butyl group, and an n-pentyl group; and a methyl group, an ethyl group, an n-propyl group, an n-butyl group, and an n-pentyl group, each substituted with a deuterium, but embodiments are not limited thereto.

In some embodiments, in Formula 1, $R_{13}$ may be selected from a hydrogen, a deuterium, —F, —Cl, —Br, —I, a cyano group, a methyl group, an ethyl group, an n-propyl group, and an n-butyl group; and a methyl group an ethyl group, an n-propyl group, and an n-butyl group, each substituted with a deuterium, but embodiments are not limited thereto.

In some embodiments, in Formula 1, $R_{13}$ may be selected from a hydrogen, a deuterium, —F, —Cl, —Br, —I, a cyano group, a methyl group, and an ethyl group; and a methyl group and an ethyl group, each substituted with a deuterium, but embodiments are not limited thereto.

In some embodiments, in Formula 1, $R_{11}$ and $R_{12}$, $R_{12}$ and $R_{13}$, $R_{13}$ and $R_{14}$, or $R_{14}$ and $R_{15}$ may be optionally linked to each other to form a condensed ring, but embodiments are not limited thereto.

In some embodiments, in Formula 1, $R_{15}$ and $R_{16}$ may be optionally linked to each other via a single bond, but embodiments are not limited thereto.

In some embodiments, in Formula 1, $R_{19}$ and $R_{20}$ may be each independently selected from a hydrogen, a deuterium, a $C_1$-$C_{10}$ alkyl group, and a $C_1$-$C_{10}$ alkyl group substituted with a deuterium.

In some embodiments, in Formula 1, $R_{19}$ and $R_{20}$ may be each independently selected from
a hydrogen;
a deuterium;
a methyl group, an ethyl group, an n-propyl group, an iso-propyl group, an n-butyl group, a sec-butyl group, an iso-butyl group, and a tert-butyl group; and
a methyl group, an ethyl group, an n-propyl group, an iso-propyl group, an n-butyl group, a sec-butyl group, an iso-butyl group, and a tert-butyl group, each substituted with a deuterium, but embodiments are not limited thereto.

In some embodiments, in Formula 1, $R_{19}$ and $R_{20}$ may be each independently selected from a hydrogen and a deuterium, but embodiments are not limited thereto.

In some embodiments, in Formula 1, $R_{19}$ may be a deuterium, and $R_{20}$ may be a hydrogen, but embodiments are not limited thereto.

In some embodiments, in Formula 1, $R_{19}$ may be a hydrogen, and $R_{20}$ may be a deuterium, but embodiments are not limited thereto.

In some embodiments, in Formula 1, $R_{19}$ and $R_{20}$ may both be a deuterium, but embodiments are not limited thereto.

In Formula 1, at least one of $R_{11}$ to $R_{20}$ may be a deuterium-containing substituent.

In some embodiments, in Formula 1, at least one of $R_{11}$, $R_{12}$, and $R_{14}$ to $R_{18}$ may be a deuterium-containing substituent, but embodiments are not limited thereto.

In some embodiments, in Formula 1, at least one of $R_{11}$, $R_{15}$, and $R_{17}$ may be a deuterium-containing substituent, but embodiments are not limited thereto.

In some embodiments, in Formula 1, $R_{11}$ or $R_{15}$ may be a deuterium-containing substituent, but embodiments are not limited thereto.

In some embodiments, in Formula 1, $R_{11}$ and $R_{15}$ may be each independently a deuterium-containing substituent, but embodiments are not limited thereto.

In some embodiments, in Formula 1, $R_{11}$, $R_{15}$, and $R_{17}$ may be each independently a deuterium-containing substituent, but embodiments are not limited thereto.

In the present specification, the term "deuterium-containing substituent" refers to a deuterium or a substituent that contains at least one deuterium. For example, a deuterium-containing substituent may refer to a substituent that is obtained by substituting at least one hydrogen atom in a substituent such as a $C_1$-$C_{30}$ alkyl group, a $C_6$-$C_{30}$ aryl group, or the like as described above with a deuterium atom.

In some embodiments, in Formula 1, the deuterium-containing substituent may be selected from
a deuterium; and
a $C_1$-$C_{10}$ alkyl group substituted with a deuterium, but embodiments are not limited thereto.

In some embodiments, in Formula 1, the deuterium-containing substituent may be selected from
a deuterium; and
a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with a deuterium, but embodiments are not limited thereto.

In some embodiments, in Formula 1, the deuterium-containing substituent may be selected from
a deuterium; and
a methyl group, an ethyl group, an n-propyl group, an iso-propyl group, an n-butyl group, a sec-butyl group, an iso-butyl group, and a tert-butyl group, each substituted with a deuterium, but embodiments are not limited thereto.

In some embodiments, in Formula 1, the deuterium-containing substituent may be selected from
-D, —$CH_2D$, —$CHD_2$, —$CD_3$, —$CH_2CH_2D$, —$CH_2CHD_2$, —$CH_2CD_3$, —$CHDCH_3$, —$CHDCH_2D$, —$CHDCHD_2$, —$CHDCD_3$, —$CD_2CH_3$, —$CD_2CH_2D$, —$CD_2CHD_2$, —$CD_2CD_3$, —$CH_2CH_2CH_2D$, —$CH_2CH_2CHD_2$, —$CH_2CH_2CD_3$, —$CH_2CHDCH_3$, —$CH_2CHDCH_2D$, —$CH_2CHDCHD_2$, —$CH_2CHDCD_3$, —$CH_2CD_2CH_3$, —$CH_2CD_2CH_2D$, —$CH_2CD_2CHD_2$, —$CH_2CD_2CD_3$, —$CHDCH_2CH_2D$, —$CHDCH_2CHD_2$, —$CHDCH_2CD_3$, —$CHDCHDCH_3$, —$CHDCHDCH_2D$, —$CHDCHDCHD_2$, —$CHDCHDCD_3$, —$CHDCD_2CH_3$, —$CHDCD_2CH_2D$, —$CHDCD_2CHD_2$, —$CHDCD_2CD_3$, —$CD_2CH_2CH_2D$, —$CD_2CH_2CHD_2$, —$CD_2CH_2CD_3$, —$CD_2CHDCH_3$, —$CD_2CHDCH_2D$, —$CD_2CHDCHD_2$, —$CD_2CHDCD_3$, —$CD_2CD_2CH_3$, —$CD_2CD_2CH_2D$, —$CD_2CD_2CHD_2$, —$CD_2CD_2CD_3$, —$CH(CH_3)(CH_2D)$, —$CH(CH_3)(CHD_2)$, —$CH(CH_2D)(CH_2D)$, —$CH(CH_3)(CD_3)$, —$CH(CHD_2)(CHD_2)$, —$CH(CH_2D)(CD_3)$, —$CH(CHD_2)(CHD_2)$, —$CH(CH_2D)(CD_3)$, —$CH(CD_3)_2$, —$CD(CH_3)_2$, —$CD(CH_3)(CH_2D)$, —$CD(CH_3)(CHD_2)$, —$CD(CH_2D)(CH_2D)$, —$CD(CH_3)(CD_3)$, —$CD(CHD_2)(CHD_2)$, —$CD(CH_2D)(CD_3)$, —$CD(CHD_2)(CHD_2)$, —$CD(CHD_2)(CD_3)$, —$CD(CD_3)_2$, and —$C(CD_3)_3$, but embodiments are not limited thereto.

In some embodiments, in Formula 1, the deuterium-containing substituent may be selected from
-D, —$CD_3$, —$CD(CH_3)_2$, —$CD(CD_3)_2$, and —$C(CD_3)_3$, but embodiments are not limited thereto.

In Formula 1, a moiety represented by

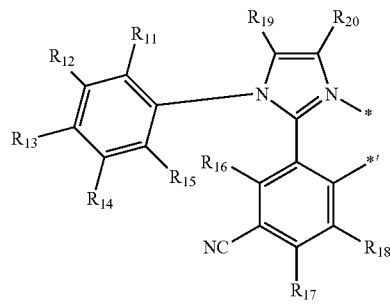

(wherein * and *' each indicate a binding site to Ir in Formula 1) may include at least one deuterium.

Whether the moiety represented by

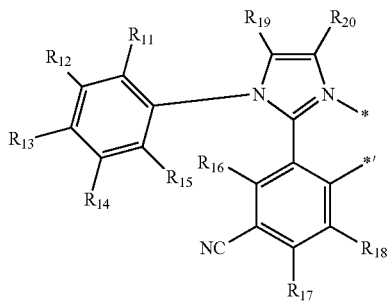

includes a deuterium or not may be identified by analyzing the $^1$H NMR spectrum or molecular weight measured using a molecular weight measurement device such as a matrix-assisted laser desorption-ionization-time-of-flight mass spectrometer.

For example, a compound (hereinafter referred to as a "first reference compound") having a backbone that is identical to the backbone of the organometallic compound represented by Formula 1 but including no deuterium atom may be prepared. The $^1$H NMR spectra of the first reference compound and the organometallic compound represented by Formula 1 may be obtained. Then, by comparing integral values of signals at a certain ppm in the obtained spectra of the first reference compound and the organometallic compound with each other, the number of hydrogen atoms at certain positions (i.e., hydrogen atoms bound to certain carbons) in the organometallic compound represented by Formula 1 that are substituted with deuterium may be determined.

Alternatively, existence of a compound (hereinafter referred to as a "second reference compound") having a backbone that is identical to the backbone of the organometallic compound represented by Formula 1, wherein all hydrogen atoms are substituted with deuterium may be assumed. By comparing the calculated molecular weight of the second reference compound with the molecular weight of the organometallic compound represented by Formula 1, the number of hydrogen atoms in the organometallic compound represented by Formula 1 that are substituted with deuterium may be determined.

In some embodiments, the organometallic compound represented by Formula 1 may have a deuteration degree, which is determined by Equation 1, of 50% or more, but embodiments are not limited thereto:

$$\text{Deuteration degree (\%)} = n_{D1}/(n_{H1}+n_{D1}) \times 100 \quad \text{Equation 1}$$

wherein in Equation 1, $n_{H1}$ indicates the total number of hydrogens included in the deuterium-containing substituents of the organometallic compound represented by Formula 1;

$n_{D1}$ indicates the total number of deuteriums included in the deuterium-containing substituents of the organometallic compound represented by Formula 1.

In some embodiments, a deuteration degree determined by Equation 1 of the organometallic compound represented by Formula 1 may be 70% or more, but embodiments are not limited thereto.

In some embodiments, a deuteration degree determined by Equation 1 of the organometallic compound represented by Formula 1 may be 90% or more, but embodiments are not limited thereto.

In Formula 1, n11 indicates the number of ligands represented by

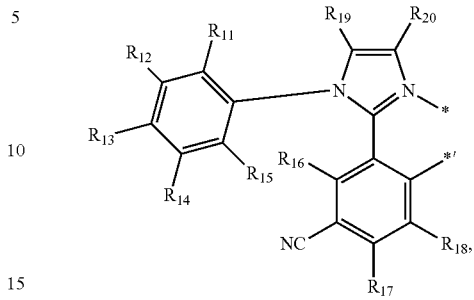

and n11 may be selected from 1, 2, and 3. When n11 is 2 or more, ligands represented by

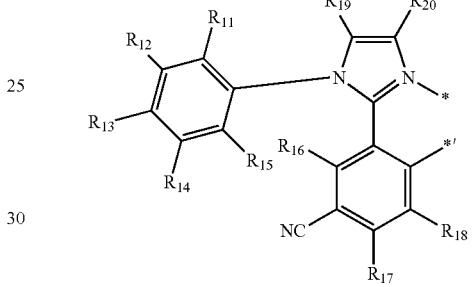

may be identical to or different from each other.

In some embodiments, in Formula 1, n11 may be 3, but embodiments are not limited thereto.

In Formula 1, $L_{11}$ may be selected from a monodentate ligand and a bidentate ligand.

In some embodiments, in Formula 1, $L_{11}$ may be selected from a monodentate ligand, and $L_{11}$ may be selected from I$^-$, Br$^-$, Cl$^-$, a sulfide, a nitrate, an azide, a hydroxide, a cyanate, an isocyanate, a thiocyanate, water, acetonitrile, a pyridine, ammonia, carbon monoxide, P(Ph)$_3$, P(Ph)$_2$CH$_3$, PPh(CH$_3$)$_2$, and P(CH$_3$)$_3$, but embodiments are not limited thereto.

In some embodiments, in Formula 1, $L_{11}$ may be selected from bidentate ligands, and $L_{11}$ may be selected from an oxalate, an acetylacetonate, a picolinic acid, a 1,2-bis(diphenylphosphino)ethane, a 1,1-bis(diphenylphosphino)methane, a glycinate, an ethylenediamine, and one of Formulae 4-1 to 4-4, but embodiments are not limited thereto:

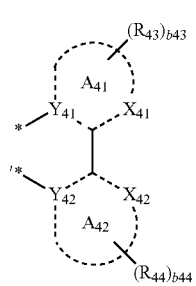

4-1

-continued 4-2

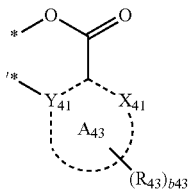

4-3

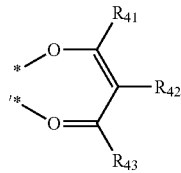

4-4

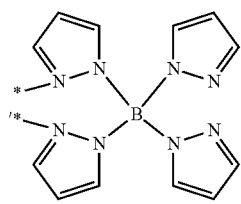

wherein in Formulae 4-1 to 4-4, $X_{41}$ may be selected from $CR_{41}$ and a nitrogen atom (N); $X_{42}$ may be selected from $CR_{42}$ and N;

$Y_{41}$ and $Y_{42}$ may be each independently selected from a carbon (C) atom and N;

$A_{41}$ to $A_{43}$ may be each independently selected from a $C_3$-$C_{10}$ cycloalkane, a $C_1$-$C_{10}$ heterocycloalkene, a $C_3$-$C_{10}$ cycloalkene, a $C_1$-$C_{10}$ heterocycloalkene, a $C_6$-$C_{10}$ arene, a $C_1$-$C_{10}$ heteroarene, a non-aromatic condensed polycycle, and a non-aromatic condensed heteropolycycle;

$R_{41}$ to $R_{44}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_{41}$)($Q_{42}$)($Q_{43}$); wherein b43 and b44 may be each independently an integer selected from 1 to 5;

$Q_{41}$ to $Q_{43}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and

* and *' each independently indicate a binding site to Ir in Formula 1.

In some embodiments, in Formula 1, $L_{11}$ may be represented by one of Formulae 4-1 to 4-4;

$A_{41}$ to $A_{43}$ may be each independently selected from a benzene, a naphthalene, a fluorene, a spiro-fluorene, an indene, a furan, a thiophene, a carbazole, a benzofuran, a benzothiophene, a dibenzofuran, a dibenzothiophene, a pyrrole, an imidazole, a pyrazole, a thiazole, an isothiazole, an oxazole, an isoxazole, a triazole, a pyridine, a pyrazine, a pyrimidine, a quinoline, an isoquinoline, a benzoquinoline, a quinoxaline, a quinazoline, a naphthyridine, a benzoimidazole, a benzoxazole, an isobenzoxazole, an oxadiazole, and a triazine;

$R_{41}$ to $R_{44}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —Si($Q_{41}$)($Q_{42}$)($Q_{43}$); wherein b43 and b44 may be each independently an integer selected from 1 to 3;

$Q_{41}$ to $Q_{43}$ may be each independently selected from a $C_1$-$C_{10}$ alkyl group, a phenyl group, a naphthyl group, a pyridinyl group, a pyrimidinyl group, and a triazinyl group, but embodiments are not limited thereto.

In some embodiments, in Formula 1, $L_{11}$ may be represented by one of Formulae 4-1 to 4-4;

$A_{41}$ may be selected from a pyridine, an imidazole, a pyrazole, a triazole, and a tetrazole, $A_{42}$ may be selected from a benzene, a pyridine, a pyrazine, a pyrimidine, and a triazine, $A_{43}$ may be selected from a benzene and a pyridine;

$R_{41}$ to $R_{44}$ may be each independently selected from a hydrogen, —F, a cyano group, a nitro group, a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group; and a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group, each substituted with at least one selected from —F, a cyano group, and a nitro group;

b43 and b44 may be each independently an integer selected from 1 to 3, but embodiments are not limited thereto.

In some embodiments, $L_{11}$ in Formula 1 may be represented by one of Formulae 5-1 to 5-119, but embodiments are not limited thereto:

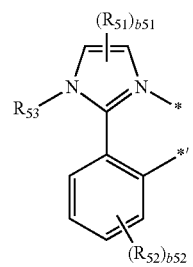

5-1

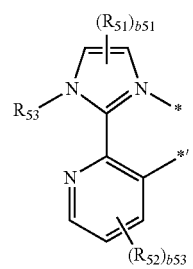

5-2

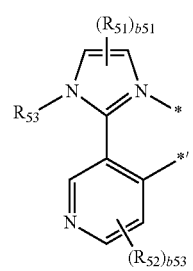

5-3

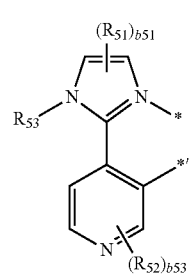

5-4

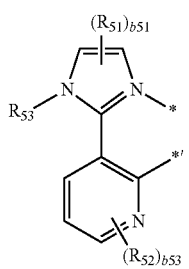
5-5
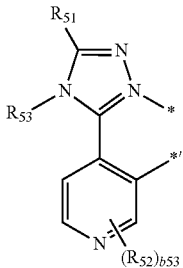
5-11
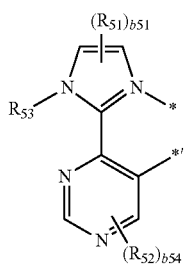
5-6
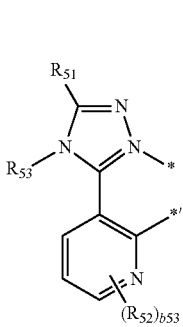
5-12
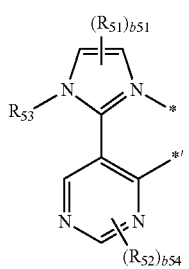
5-7
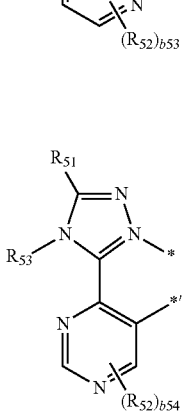
5-13
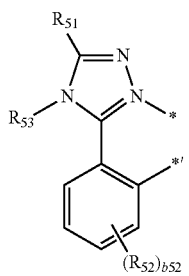
5-8
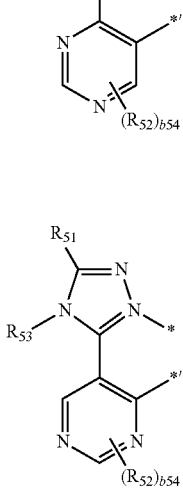
5-14
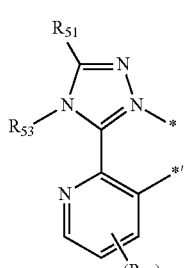
5-9
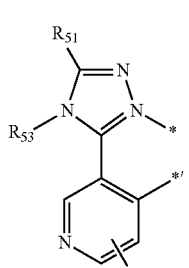
5-10
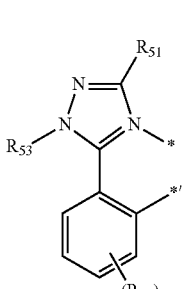
5-15

5-16
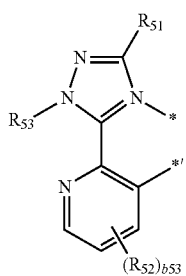
5-17
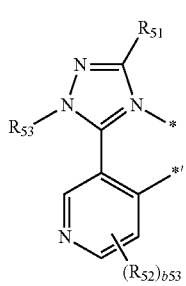
5-18
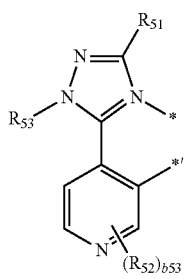
5-19
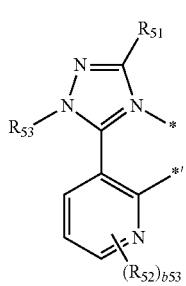
5-20
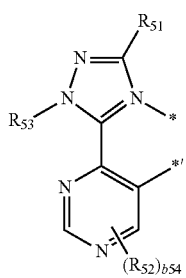
5-21
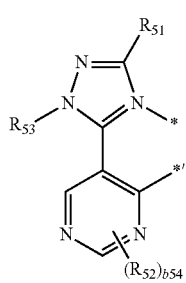
5-22
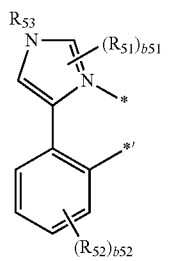
5-23
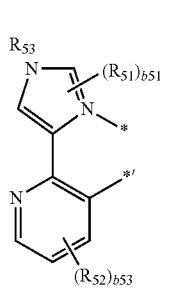
5-24
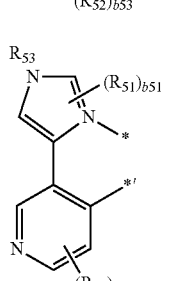
5-25
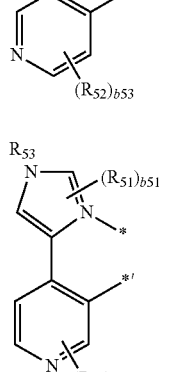
5-26
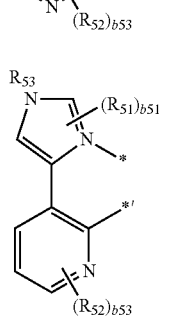

-continued
5-27 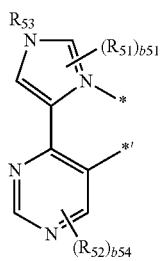
5-28 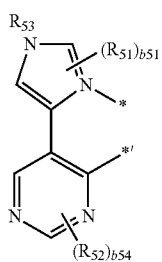
5-29 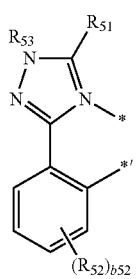
5-30 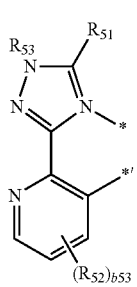
5-31 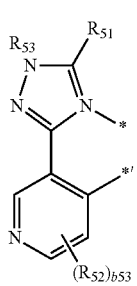
5-32 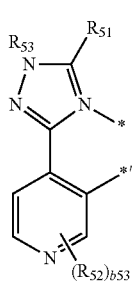
-continued
5-33 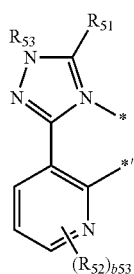
5-34 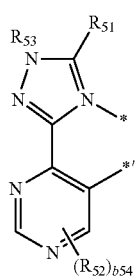
5-35 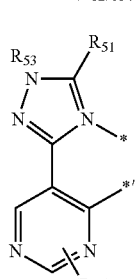
5-36 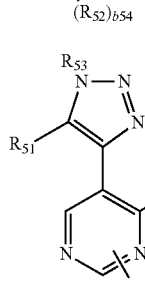
5-37 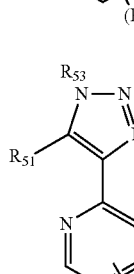
5-38 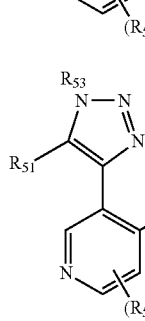

5-39 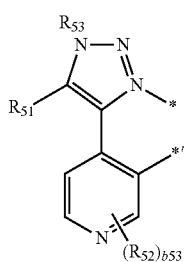
5-40 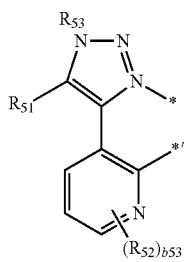
5-41 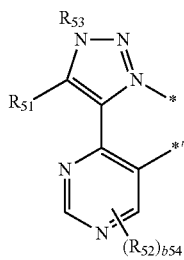
5-42 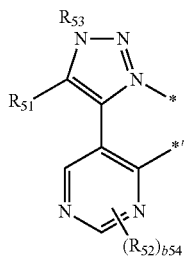
5-43 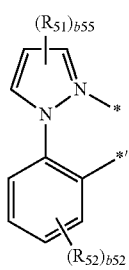
5-44 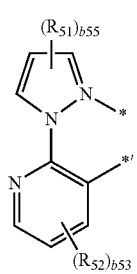
5-45 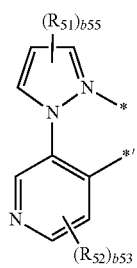
5-46 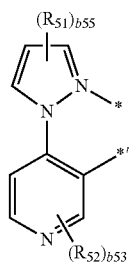
5-47 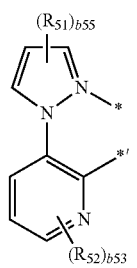
5-48 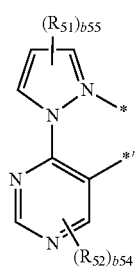
5-49 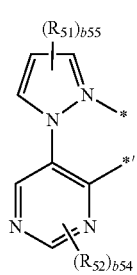
5-50 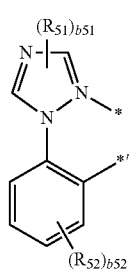

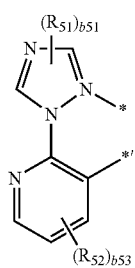
5-51
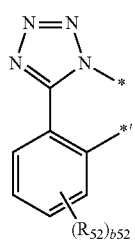
5-57
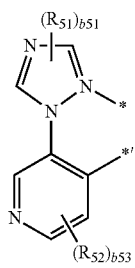
5-52
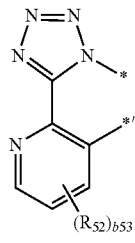
5-58
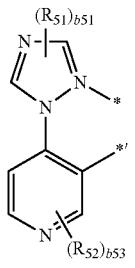
5-53
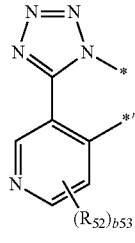
5-59
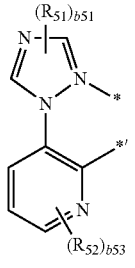
5-54
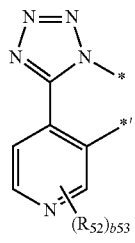
5-60
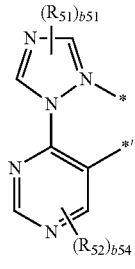
5-55
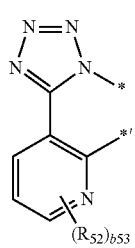
5-61
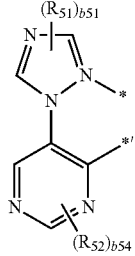
5-56
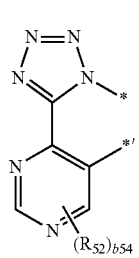
5-62

5-63 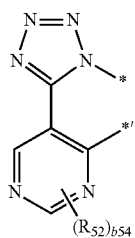
5-64 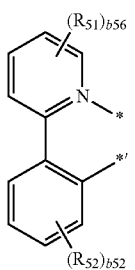
5-65 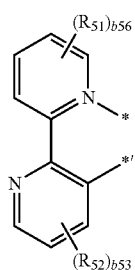
5-66 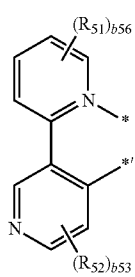
5-67 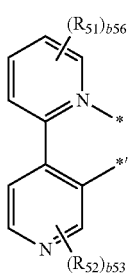
5-68 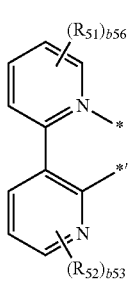
5-69 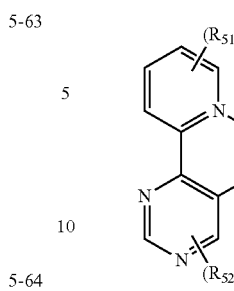
5-70 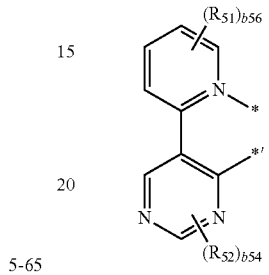
5-71 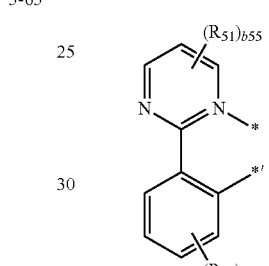
5-72 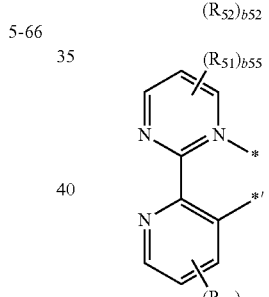
5-73 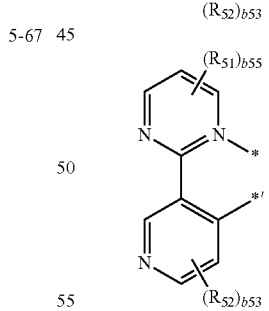
5-74 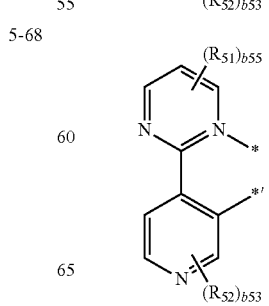

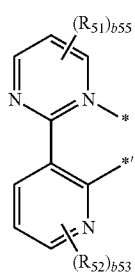
5-75
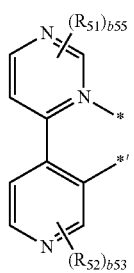
5-81
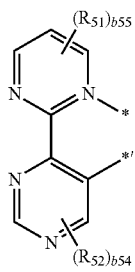
5-76
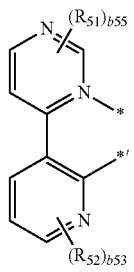
5-82
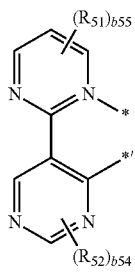
5-77
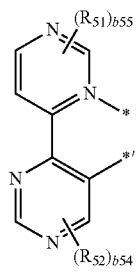
5-83
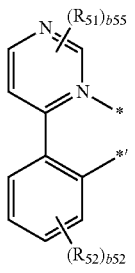
5-78
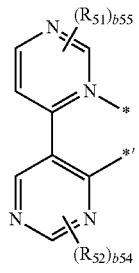
5-84
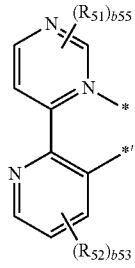
5-79
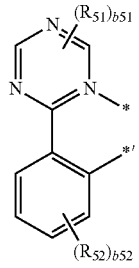
5-85
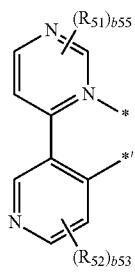
5-80
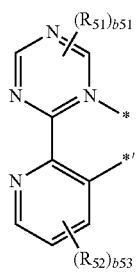
5-86

5-87
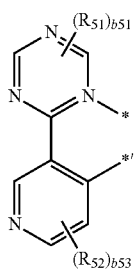
5-88
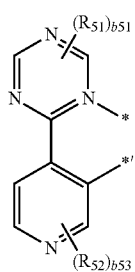
5-89
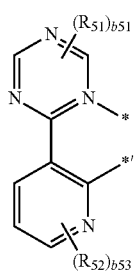
5-90
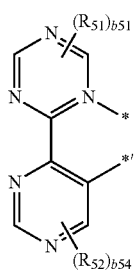
5-91
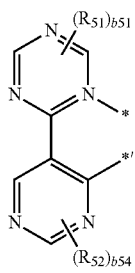
5-92
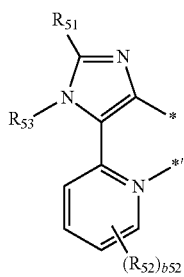
5-93
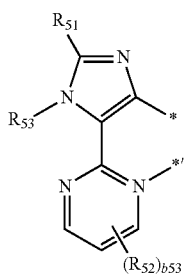
5-94
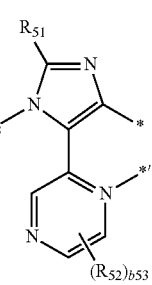
5-95
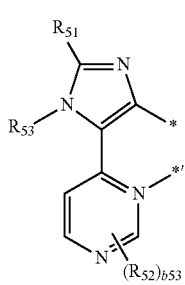
5-96
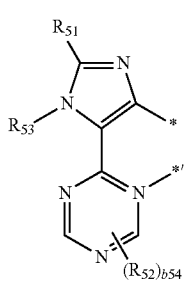
5-97
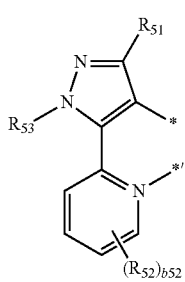

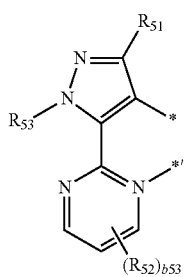
5-98
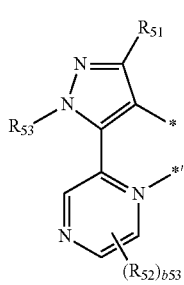
5-99
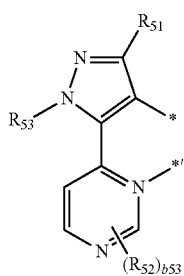
5-100
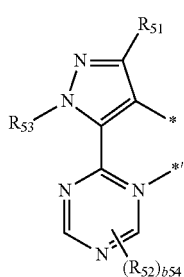
5-101
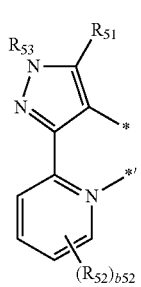
5-102
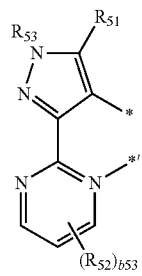
5-103
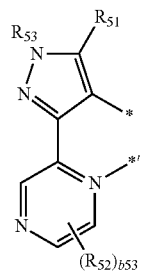
5-104
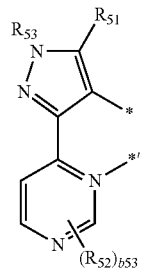
5-105
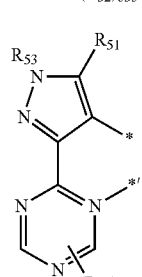
5-106
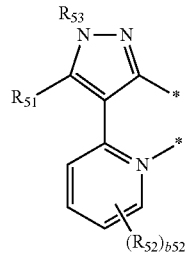
5-107
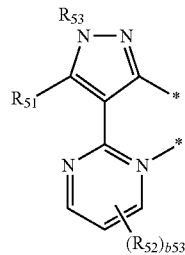
5-108

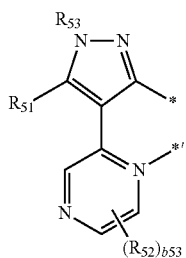
5-109

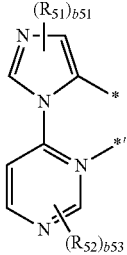
5-115

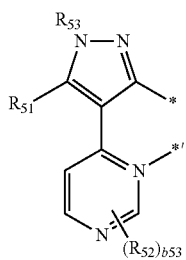
5-110

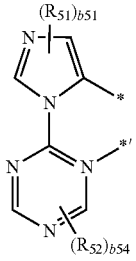
5-116

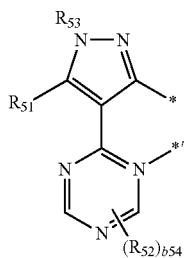
5-111

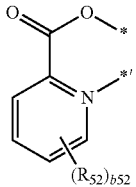
5-117

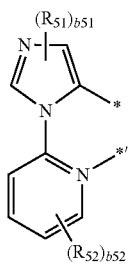
5-112

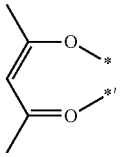
5-118

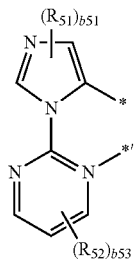
5-113

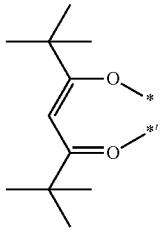
5-119

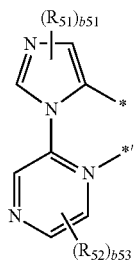
5-114 wherein in Formulae 5-1 to 5-119, $R_{51}$ to $R_{53}$ may be each independently selected from a hydrogen, —F, a cyano group, a nitro group, a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group; and a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, butoxy group, a pentoxy group, a phenyl group, a naphthyl group, a pyridinyl group, a pyrimidinyl group, a triazinyl group, a dibenzofuranyl group, and a dibenzothiophenyl group, each substituted with at least one selected from —F, a cyano group, and a nitro group;

b51 and b54 may be each independently selected from 1 and 2;

b53 and b55 may be each independently an integer selected from 1 to 3;

b52 may be an integer selected from 1 to 4; and

* and *' may be each independently a binding site to a neighboring atom.

In Formula 1, m11 indicates the number of groups $L_{11}$, and m11 may be selected from 0, 1, 2, 3, and 4. When m11 is 2 or more, a plurality of groups $L_{11}$ may be identical to or different from each other. In some embodiments, in Formula 1, m11 may be 0, but embodiments are not limited thereto.

In Formula 1, n11 and m11 may be properly controlled based on the coordination number of Ir. For example, when n11 is 3, m11 may be 0. In some embodiments, if $L_{11}$ is a bidentate ligand, when n11 is 2, m11 may be 1. In some embodiments, if $L_{11}$ is a bidentate ligand, when n11 is 1, m11 may be 2.

In some embodiments, the organometallic compound may be represented by Formula 1-1, but embodiments are not limited thereto:

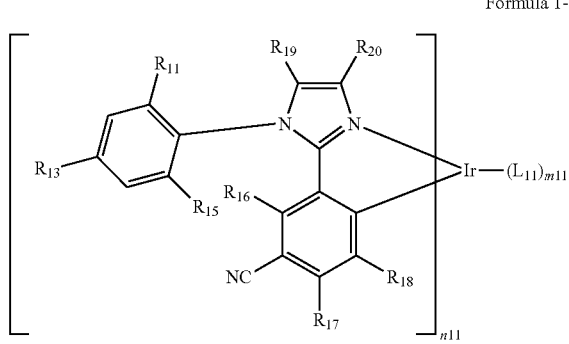

Formula 1-1 wherein in Formula 1-1, descriptions of $R_{11}$, $R_{13}$, $R_{15}$ to $R_{20}$, $L_{11}$, n11, and m11 are the same as in Formula 1.

In some embodiments, the organometallic compound may be represented by Formula 1-11, but embodiments are not limited thereto:

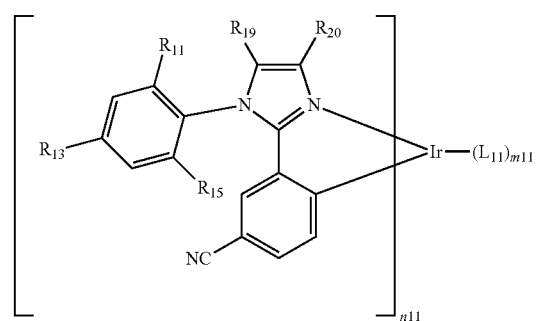

Formula 1-11 wherein in Formula 1-11, descriptions of $R_{11}$, $R_{13}$, $R_{15}$, $R_{17}$, $R_{19}$, $R_{20}$, $L_{11}$, n11, and m11 are the same as in Formula 1.

In some embodiments, the organometallic compound may be represented by one of Formulae 1-21 and 1-22, but embodiments are not limited thereto:

Formula 1-21

Formula 1-22 wherein in Formulae 1-21 and 1-22, descriptions of $R_{13}$, $R_{17}$, $R_{19}$, $R_{20}$, $L_{11}$, n11, and m11 are the same as in Formula 1; and $R_{x1}$ to $R_{x3}$ are each independently understood by referring to the descriptions of the deuterium-containing substituent in Formula 1.

In some embodiments, the organometallic compound may be selected from Compounds 1 to 24, but embodiments are not limited thereto:

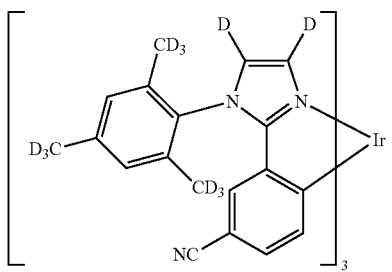
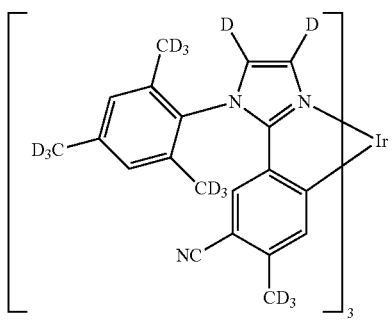
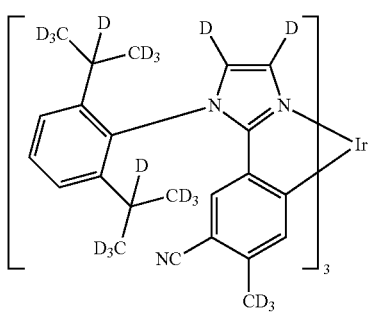
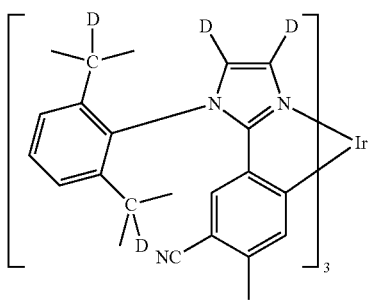
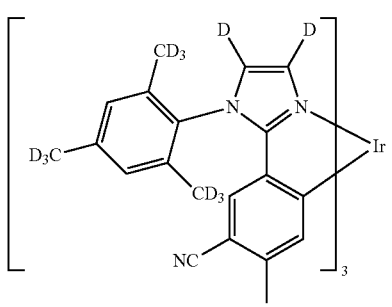
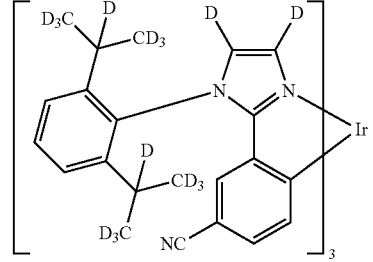
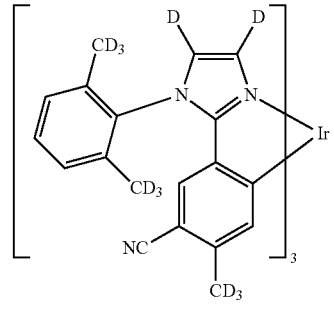
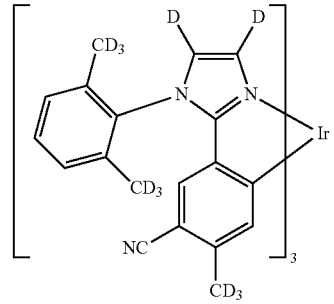
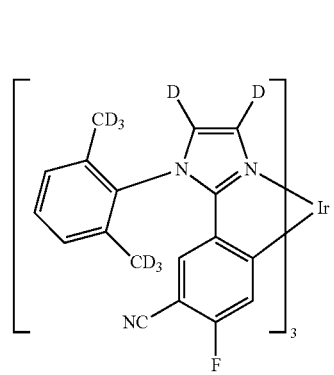
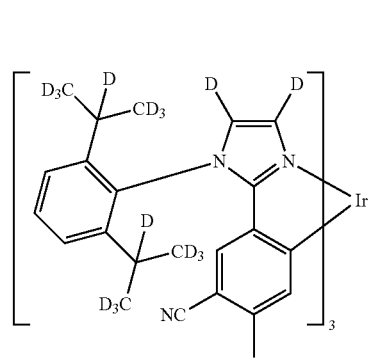

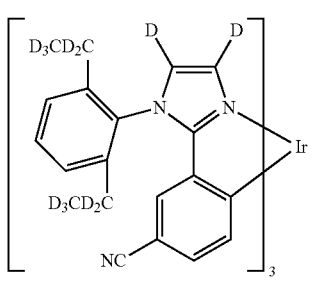
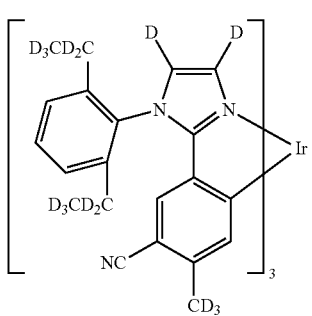
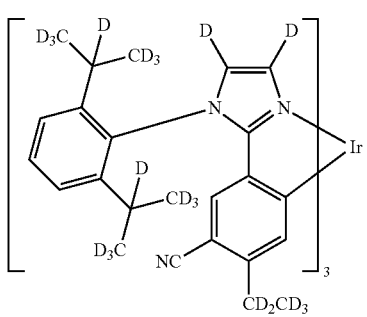
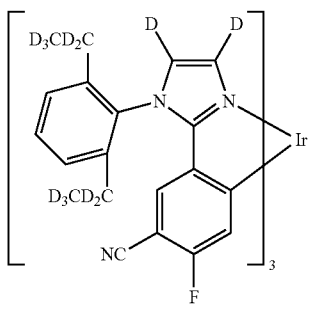
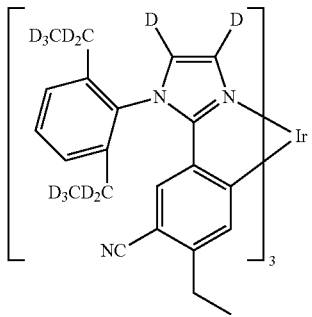
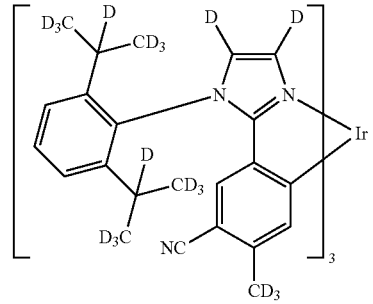
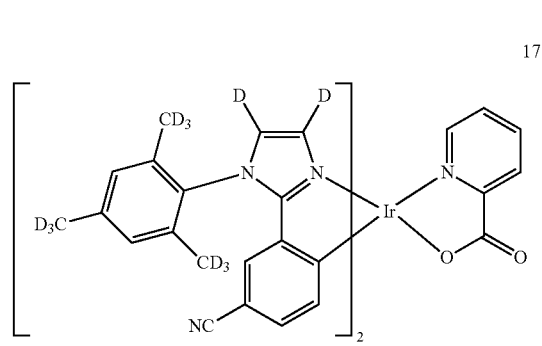
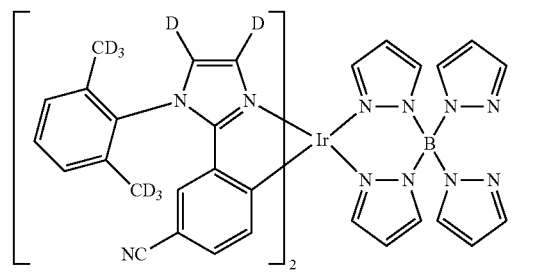
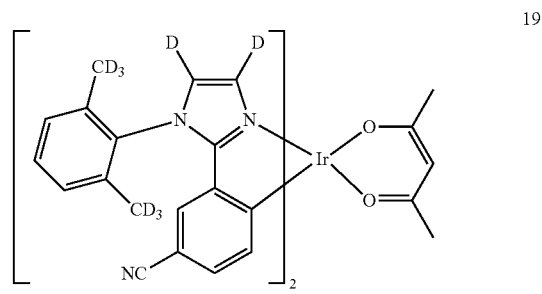
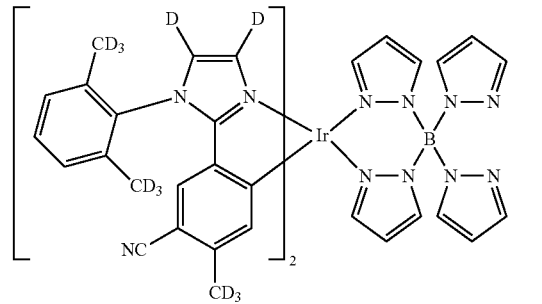

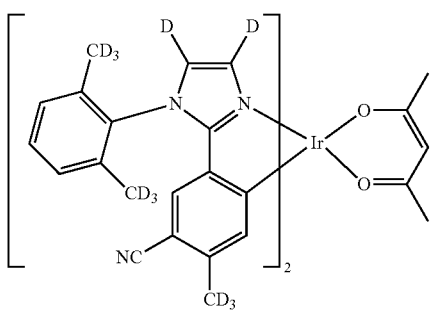

21

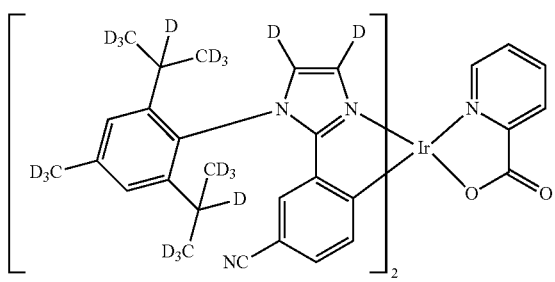

22

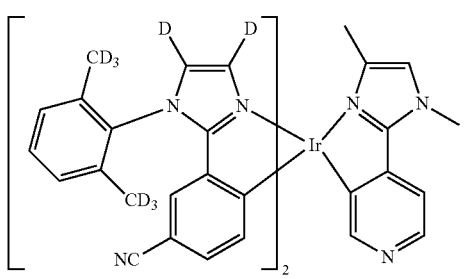

23

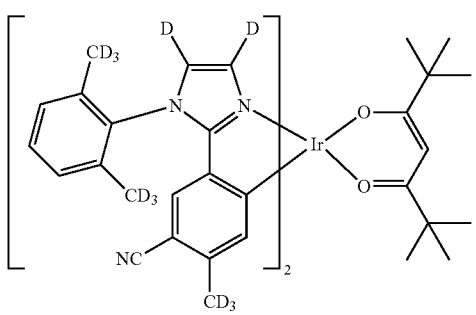

24

A maximum emission wavelength of the organometallic compound may be 440 nm to 465 nm or less. When the maximum emission wavelength thereof is 440 nm to 465 nm or less, the organic light-emitting device may provide a deep blue emission color.

The organometallic compound represented by Formula 1 may provide a deep blue emission color by including "a cyano group" at a "specific position".

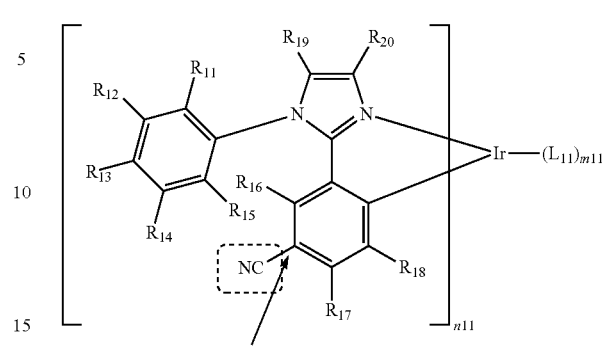

Para-position with respect to Ir-carbon bonding site

As shown in Formula 1', when a cyano group is at a para position with respect to a Ir—C binding site, the organometallic compound of Formula 1 may have a deep highest occupied molecular orbital (HOMO) energy level. Accordingly, the organometallic compound of Formula 1 may have a high triplet energy level due to an increased band gap, and thus provide a deep blue emission color.

The organometallic compound represented by Formula 1 essentially includes "a deuterium", thereby having improved thermal stability. Particularly, a carbon-deuterium single bond has a stronger bond strength and shorter bond length than a carbon-hydrogen single bond. Thus, an organometallic compound including a deuterium has high thermal stability, compared to the thermal stability of an organometallic compound that does not include a deuterium. Therefore, when storing and/or operating an organic light-emitting device including the organometallic compound represented by Formula 1, dissociation of the organometallic compound into radicals due to heat and/or an electric field occurs substantially slowly. Thus, the organic light-emitting device including the organometallic compound may have improved lifespan characteristics.

The HOMO energy level, lowest unoccupied molecular orbital (LUMO) energy level, T1 energy level, and maximum emission wavelength of some organometallic compounds represented by Formula 1 were evaluated by using Gaussian 09 that performs molecular structure optimizations according to density functional theory (DFT) based on B3LYP. The results thereof are shown in Table 1.

TABLE 1

| Compound No. | HOMO (eV) | LUMO (eV) | T1 (eV) | $\lambda_{max}$ (nm) |
|---|---|---|---|---|
| 6 | −5.28 | −1.18 | 2.78 | 446 |
| 7 | −5.28 | −1.17 | 2.78 | 445 |
| 16 | −5.18 | −1.05 | 2.79 | 444 |
| A | −4.90 | −0.89 | 2.71 | 458 |
| B | −5.18 | −1.50 | 2.48 | 499 |
| C | −5.14 | −1.47 | 2.39 | 520 |
| D | −5.28 | −1.18 | 2.78 | 446 |
| E | −5.28 | −1.17 | 2.78 | 445 |
| F | −5.18 | −1.05 | 2.79 | 444 |

6
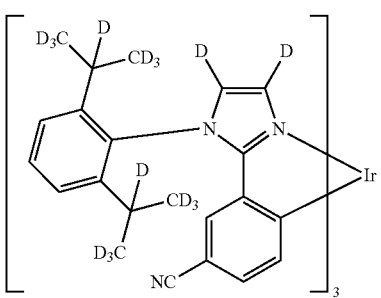

5
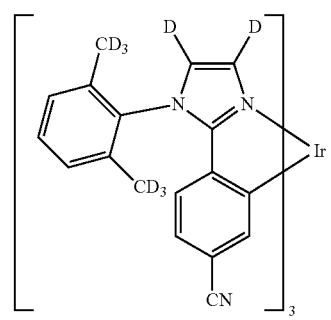
C

7
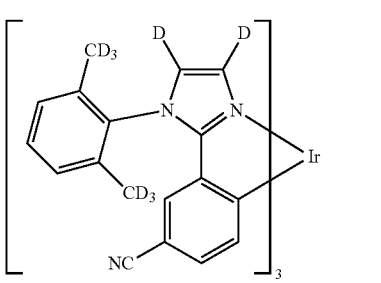

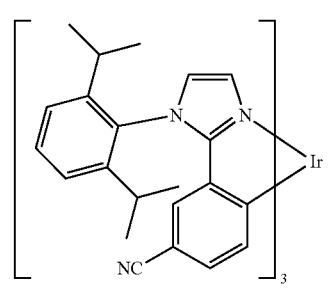
D

16
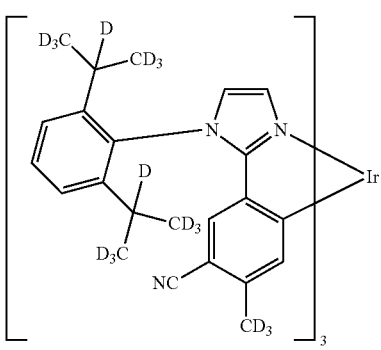

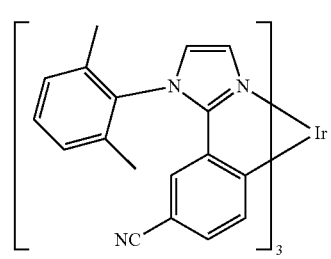
E

A
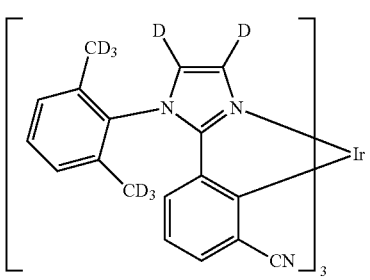

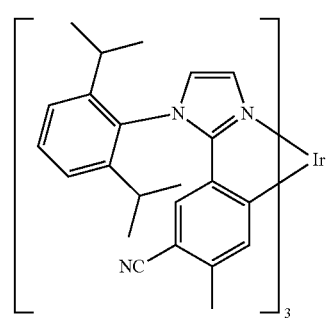
F

B
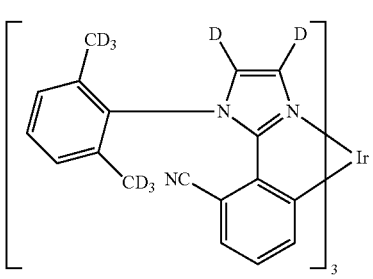

An organometallic compound that does not include deuterium may be synthesized by a method similar to the method of preparation of the organometallic compound of Formula 1. In this regard, according to another aspect of the present disclosure, a composition containing an organometallic compound represented by Formula 2 (hereinafter referred to as a "second organometallic compound") as well as the organometallic compound represented by Formula 1 (hereinafter referred to as a "first organometallic compound") may be provided:

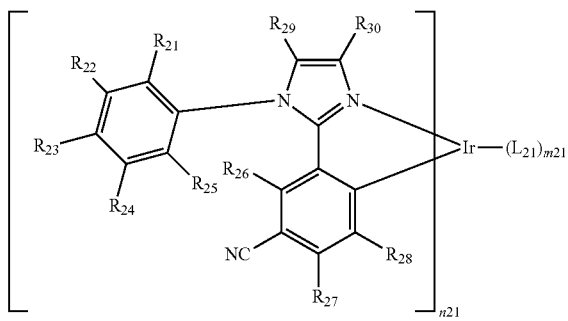

Formula 2 wherein in Formula 2, $R_{21}$, $R_{22}$, and $R_{24}$ to $R_{28}$ may be each independently selected from a hydrogen, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group.

In some embodiments, in Formula 2, $R_{21}$, $R_{22}$, and $R_{24}$ to $R_{28}$ may be each independently selected from a hydrogen, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a substituted or unsubstituted $C_1$-$C_{10}$ alkyl group, but embodiments are not limited thereto.

In some embodiments, in Formula 2, $R_{21}$, $R_{22}$, and $R_{24}$ to $R_{28}$ may be each independently selected from a hydrogen, —F, —Cl, —Br, —I, a cyano group, and a $C_1$-$C_{10}$ alkyl group; and
a $C_1$-$C_{10}$ alkyl group substituted with at least one selected from —F, —Cl, —Br, —I, and a cyano group; but embodiments are not limited thereto.

In some embodiments, in Formula 2, $R_{21}$, $R_{22}$, and $R_{24}$ to $R_{28}$ may be each independently selected from a hydrogen, —F, —Cl, —Br, —I, a cyano group, and a $C_1$-$C_{10}$ alkyl group, but embodiments are not limited thereto.

In some embodiments, in Formula 2, $R_{21}$, $R_{22}$, and $R_{24}$ to $R_{28}$ may be each independently selected from a hydrogen, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, but embodiments are not limited thereto.

In some embodiments, in Formula 2, $R_{21}$, $R_{22}$, and $R_{24}$ to $R_{28}$ may be each independently selected from a hydrogen, —F, —Cl, —Br, —I, a cyano group, a methyl group, an ethyl group, an n-propyl group, an iso-propyl group, an n-butyl group, a sec-butyl group, an iso-butyl group, and a tert-butyl group, but embodiments are not limited thereto.

In some embodiments, in Formula 2, $R_{21}$, $R_{25}$, and $R_{27}$ may be each independently selected from
a hydrogen, —F, —Cl, —Br, —I, a cyano group, a methyl group, an ethyl group, an n-propyl group, an iso-propyl group, an n-butyl group, a sec-butyl group, an iso-butyl group, and a tert-butyl group, but embodiments are not limited thereto.

In some embodiments, in Formula 2, $R_{21}$ or $R_{25}$ may be selected from a hydrogen, —F, —Cl, —Br, —I, a cyano group, a methyl group, an ethyl group, an n-propyl group, an iso-propyl group, an n-butyl group, a sec-butyl group, an iso-butyl group, and a tert-butyl group, but embodiments are not limited thereto.

In some embodiments, in Formula 2, $R_{21}$ and $R_{25}$ may be each independently selected from a hydrogen, —F, —Cl, —Br, —I, a cyano group, a methyl group, an ethyl group, an n-propyl group, an iso-propyl group, an n-butyl group, a sec-butyl group, an iso-butyl group, and a tert-butyl group, but embodiments are not limited thereto.

In some embodiments, in Formula 2, $R_{23}$ may be selected from a hydrogen, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ linear alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group.

In some embodiments, in Formula 2, $R_{23}$ may be selected from a hydrogen, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, and a substituted or unsubstituted $C_1$-$C_{10}$ linear alkyl group, but embodiments are not limited thereto.

In some embodiments, in Formula 2, $R_{23}$ may be selected from a hydrogen, —F, —Cl, —Br, —I, a cyano group, a $C_1$-$C_{10}$ linear alkyl group; and
a $C_1$-$C_{10}$ linear alkyl group substituted with at least one selected from —F, —Cl, —Br, —I, and a cyano group; but embodiments are not limited thereto.

In some embodiments, in Formula 2, $R_{23}$ may be selected from a hydrogen, a deuterium, —F, —Cl, —Br, —I, a cyano group, and a $C_1$-$C_{10}$ linear alkyl group, but embodiments are not limited thereto.

In some embodiments, in Formula 2, $R_{23}$ may be selected from a hydrogen, a deuterium, —F, —Cl, —Br, —I, a cyano group, a methyl group, an ethyl group, an n-propyl group, an n-butyl group, and an n-pentyl group, but embodiments are not limited thereto.

In some embodiments, in Formula 2, $R_{23}$ may be selected from a hydrogen, a deuterium, —F, —Cl, —Br, —I, a cyano group, a methyl group, an ethyl group, an n-propyl group, and an n-butyl group, but embodiments are not limited thereto.

In some embodiments, in Formula 2, $R_{23}$ may be selected from a hydrogen, a deuterium, —F, —Cl, —Br, —I, a cyano group, a methyl group, and an ethyl group, but embodiments are not limited thereto.

In some embodiments, in Formula 2, $R_{21}$ and $R_{22}$, $R_{22}$ and $R_{23}$, $R_{23}$ and $R_{24}$, or $R_{24}$ and $R_{25}$ may be optionally bound to each other so as to form a condensed ring, but embodiments are not limited thereto.

In some embodiments, in Formula 2, $R_{25}$ and $R_{26}$ may be optionally bound to each other via a single bond, but embodiments are not limited thereto.

In Formula 2, $R_{29}$ and $R_{30}$ may be each independently selected from a hydrogen and a $C_1$-$C_{10}$ alkyl group.

In some embodiments, in Formula 2, $R_{29}$ and $R_{30}$ may be each independently selected from a hydrogen; and a methyl group, an ethyl group, an n-propyl group, an iso-propyl group, an n-butyl group, a sec-butyl group, an iso-butyl group, and a tert-butyl group, but embodiments are not limited thereto.

In some embodiments, in Formula 2, $R_{29}$ and $R_{30}$ may be a hydrogen, but embodiments are not limited thereto.

In Formula 2, $R_{21}$ to $R_{30}$ may be each independently a substituent containing no deuterium.

In the present specification, a non-deuterium containing substituent refers to a substituent in which any hydrogen atom therein is substituted with a deuterium atom.

In Formula 2, a moiety represented by

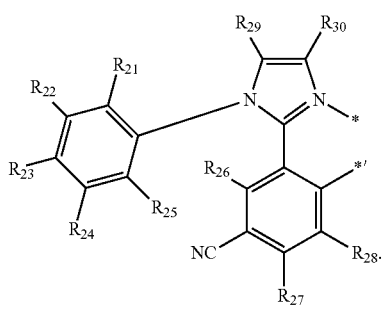

(wherein * and *' each indicate a binding site to Ir in Formula 2) may not include a deuterium atom.

In some embodiments, provided is a composition containing an organometallic compound that includes the first organometallic compound and the second organometallic compound. The organometallic compound may have a deuteration degree of 50% or more, as determined by Equation 2, but embodiments are not limited thereto:

$$\text{Deuteration degree (\%)} = n_{D2}/(n_{H2}+n_{D2}) \times 100 \quad \text{Equation 2}$$

wherein in Equation 2, $n_{H2}$ represents a sum of a total number of hydrogens in the deuterium-containing substituents of the first organometallic compound and a total number of hydrogens in substituents of the second organometallic compound that are equivalent (correspond) to the deuterium-containing substituents of the first organometallic compound; and $n_{D2}$ represents a total number of deuteriums in the deuterium-containing substituents of the first organometallic compound.

If a substituent in the dashed region in Compound 1' is a deuterium-containing substituent, the "substituents that are equivalent to the deuterium-containing substituents" used herein may include a substituent in the dashed region in Compound 1". That is, substituents bound at the same carbon location in two compounds that are the same except for having or not having an isotope thereof are defined as "equivalent" substituents.

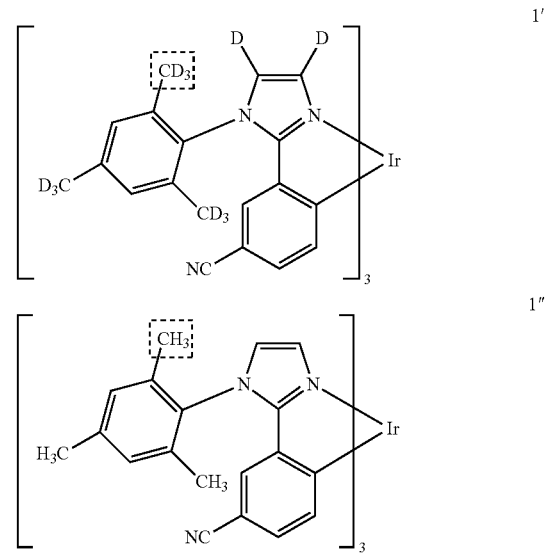

For example, when the first organometallic compound includes two deuterium-containing substituents, $n_{D2}$ indicates the number of all deuterium atoms included in the two deuterium-containing substituents of the first organometallic compound. In addition, $n_{H2}$ indicates the total number of hydrogens included in the two deuterium-containing substituents of the first organometallic compound and the total number of hydrogens included in substituents of the second organometallic compound corresponding to the two deuterium-containing substituents of the first organometallic compound.

In some embodiments, the deuteration degree may be 70% or more, 90% or more, 95% or more, 96% or more, 97% or more, 98% or more, or 99% or more, but embodiments are not limited thereto.

A method of synthesizing the organometallic compound represented by Formula 1 may be apparent to one of ordinary skill in the art by referring to Synthesis Examples used herein. The composition containing the organometallic compound may be obtained as a result of imperfect deuteration taken place during the synthesis of the organometallic compound represented by Formula 1, not by further addition at least one second organometallic compound.

Therefore, the organometallic compound represented by Formula 1 or the composition containing an organometallic compound may be used in an organic layer of an organic light-emitting device, for example, as a dopant in an emission layer of the organic layer. According to another aspect, there is provided an organic light-emitting device that includes:

a first electrode;
a second electrode; and
an organic layer disposed between the first electrode and the second electrode, wherein the organic layer includes an emission layer and the organometallic compound represented by Formula 1 or the composition containing the organometallic compound.

The organic light-emitting device may provide a high efficiency, long lifespan, and high color coordination by including an organic layer that contains the organometallic compound represented by Formula 1 or the composition containing the organometallic compound.

The organometallic compound represented by Formula 1 or the composition containing an organometallic compound may be used in a pair of electrodes in an organic light-emitting device. In some embodiments, the organometallic compound represented by Formula 1 or the composition containing the organometallic compound may be included in the emission layer. In this regard, the organometallic compound may serve as a dopant, and the emission layer may further include a host. The emission layer may emit red light, green light, or blue light.

As used herein, "(for example, the organic layer) including an organometallic compound" means that "(the organic layer) including an organometallic compound of Formula 1 above, or at least two different organometallic compounds of Formula 1 above".

For example, the organic layer may include only Compound 1 as the organometallic compound. In this regard, Compound 1 may be included in the emission layer of the organic light-emitting device. Alternatively, the organic layer may include Compound 1 and Compound 2 as the organometallic compounds. In this regard, Compound 1 and Compound 2 may be included in the same layer (for example, both Compound 1 and Compound 2 may be included in the emission layer).

The first electrode may be anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example,
the first electrode may be an anode,
the second electrode may be a cathode, and
the organic layer may include:
i) a hole-transport region disposed between the first electrode and the emission layer, wherein the hole-transport region includes at least one selected from a hole injection layer, a hole-transport layer, and an electron blocking layer; and
ii) an electron-transport region disposed between the emission layer and the second electrode, wherein the electron-transport region includes at least one selected from a hole blocking layer, an electron transport layer, and an electron injection layer.

As used herein, the term the "organic layer" refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an exemplary embodiment. Hereinafter, a structure and a method of manufacturing the organic light-emitting device 10 according to an exemplary embodiment will be described with reference to FIG. 1. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by vacuum-depositing or sputtering a material for forming the first electrode 11 on the substrate. The first electrode 11 may be an anode. The material for the first electrode 11 may be selected from materials with a high work function for an easy hole injection. The first electrode 11 may be a reflective electrode, a semi-transmissive electrode, or a transmissive electrode. The material for the first electrode 11 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag).

The first electrode 11 may have a single layer structure or a multi-layer structure including a plurality of layers. For example, the first electrode 11 may have a triple-layer structure of ITO/Ag/ITO, but embodiments are not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, hole transport layer, electron blocking layer, and buffer layer.

The hole transport region may only include a hole injection layer or a hole transport layer. Alternatively, the hole transport region may include a structure in which a hole injection layer/a hole transport layer or a hole injection layer/a hole transport layer/an electron blocking layer are sequentially layered on the first electrode 11.

When the hole transport region includes a hole injection layer, the hole injection layer may be formed on the first electrode 11 by using various methods such as vacuum-deposition, spin coating, casting, and Langmuir-Blodgett (LB) methods.

When a hole injection layer is formed by vacuum-deposition, for example, the vacuum-deposition may be performed at a deposition temperature in a range of about 100° C. to about 500° C., at a vacuum degree in a range of about $10^{-8}$ to about $10^{-3}$ torr, and at a deposition rate in a range of about 0.01 Angstroms per second (Å/sec) to about 100 Å/sec, though the conditions may vary depending on a compound that is used as a hole injection material and a structure and thermal properties of a desired hole injection layer, but embodiments are not limited thereto.

When a hole injection layer is formed by spin coating, the spin coating may be performed at a coating rate in a range of about 2000 revolutions per minute (rpm) to about 5,000 rpm, and at a temperature in a range of about 80° C. to 200° C. for removing a solvent after the spin coating, though the conditions may vary depending on a compound that is used as a hole injection material and a structure and thermal properties of a desired HIL, but embodiments are not limited thereto.

The conditions for forming a hole transport layer and an electron blocking layer may be inferred based on the conditions for forming the hole injection layer.

The hole transport region may include at least one selected from m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201, and a compound represented by Formula 202:

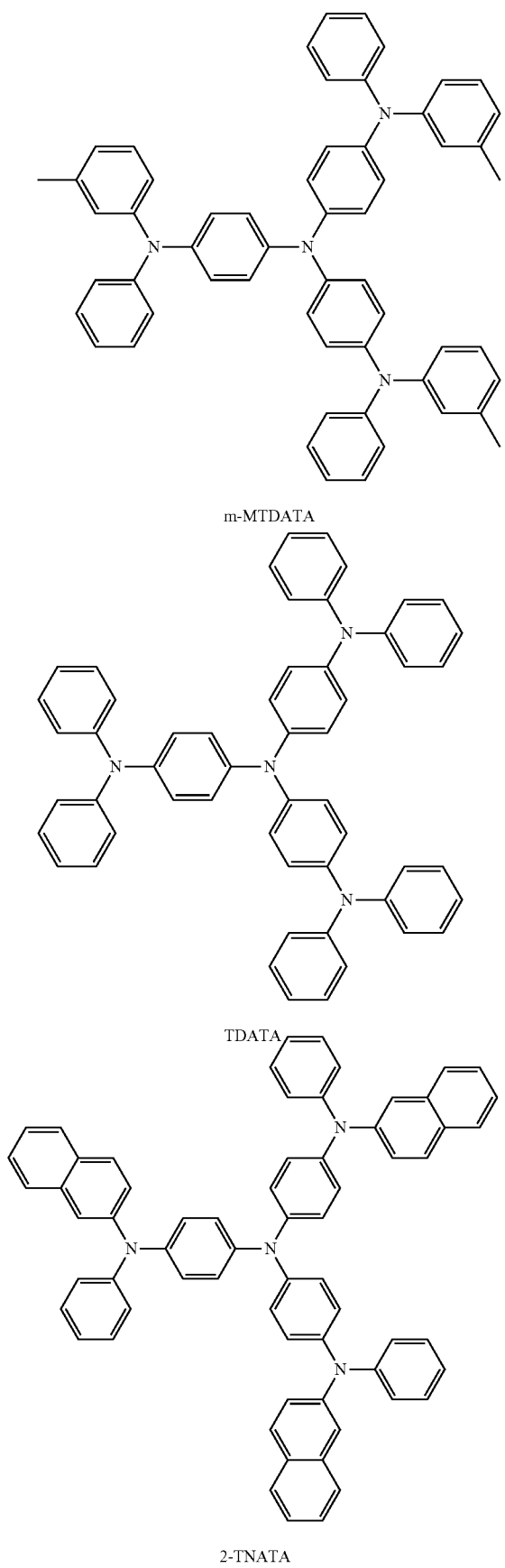
m-MTDATA
TDATA
2-TNATA
-continued
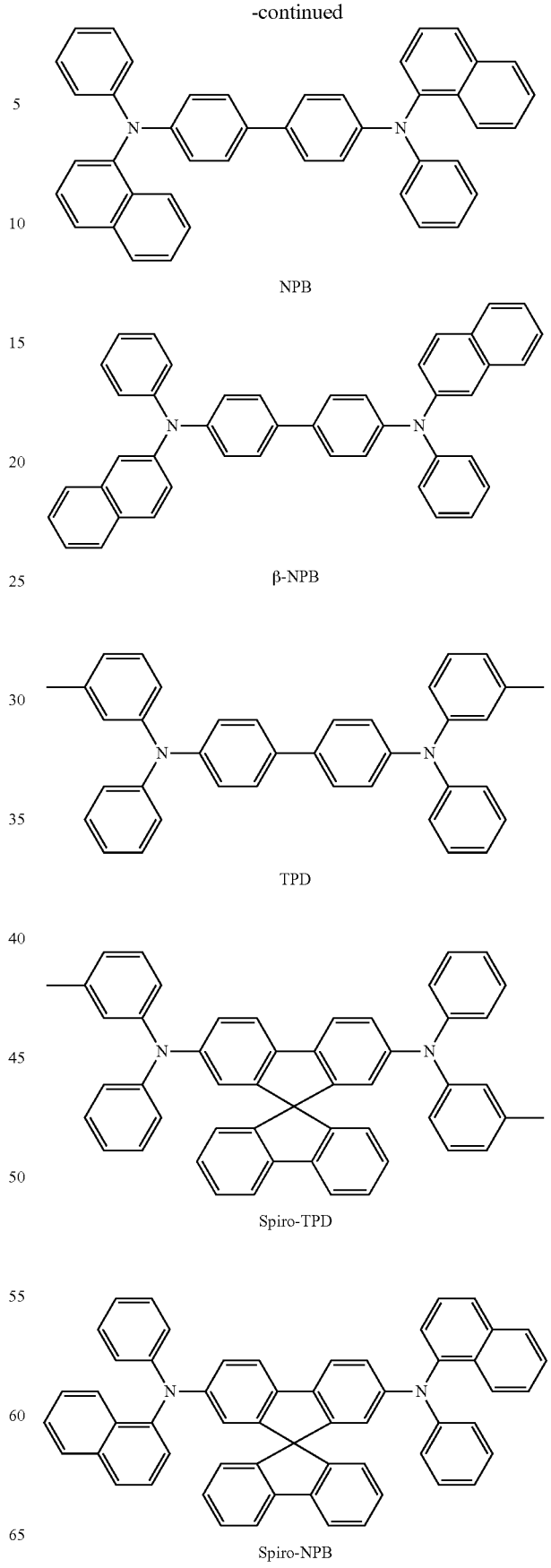
NPB
β-NPB
TPD
Spiro-TPD
Spiro-NPB

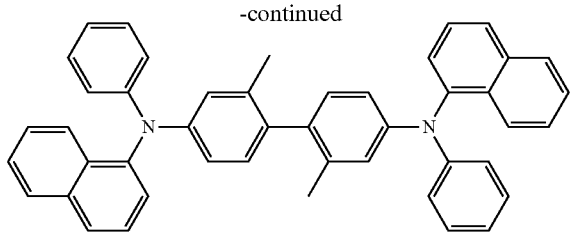

methylated NPB

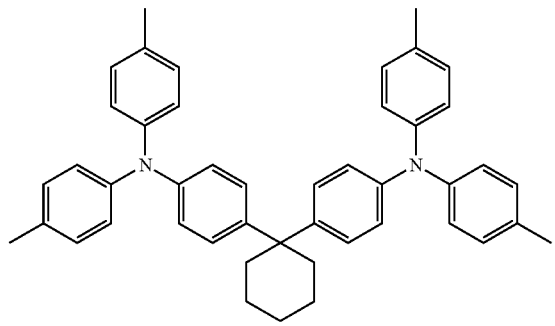

TAPC

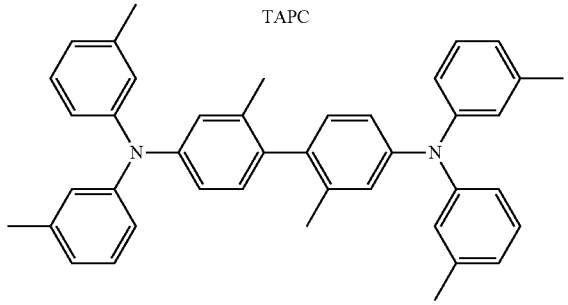

HMTPD

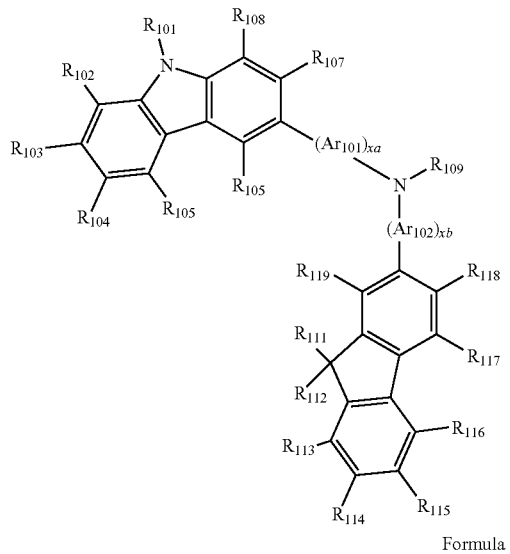

Formula 201

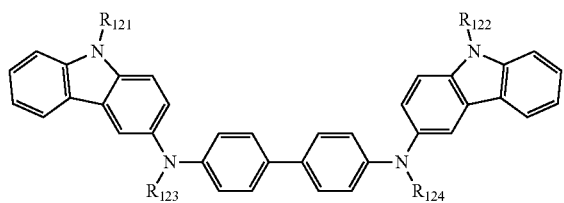

Formula 202 wherein in Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa may be each independently an integer selected from 0 to 5, and xb may be an integer selected from 0, 1, and 2. In some embodiments, xa may be 1 and xb may be 0, but embodiments are not limited thereto.

In Formula 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (such as, a methyl group, an ethyl group, a propyl group, a butyl group, a pentyl group, or a hexyl group), and a $C_1$-$C_{10}$ alkoxy group (such as, a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In some embodiments, the compound represented by Formula 201 may be represented by Formula 201A, but embodiments are not limited thereto:

Formula 201A

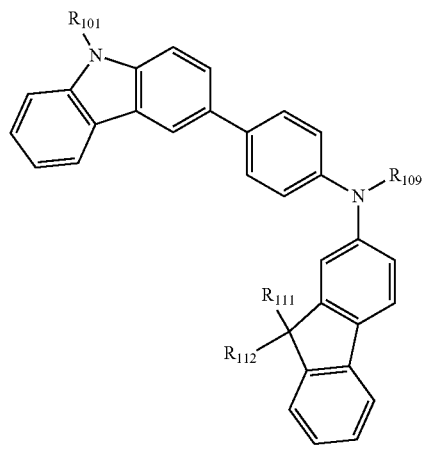

Descriptions of $R_{101}$, $R_{111}$, $R_{112}$, and $R_{109}$ in Formula 201A are the same as described above.

For example, the compound represented by Formula 201 and the compound represented by Formula 202 may include Compounds HT1 to HT20, but embodiments are not limited thereto:

HT1

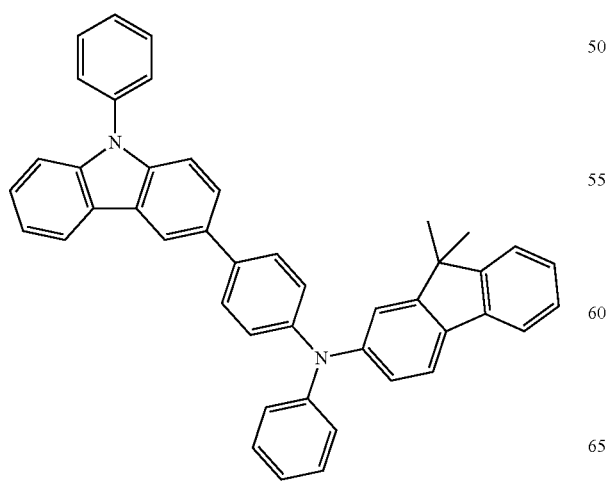

HT2

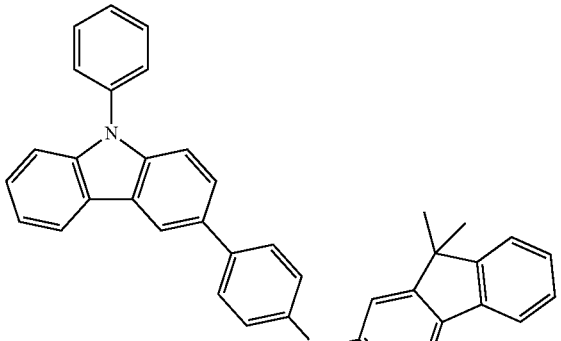

HT3

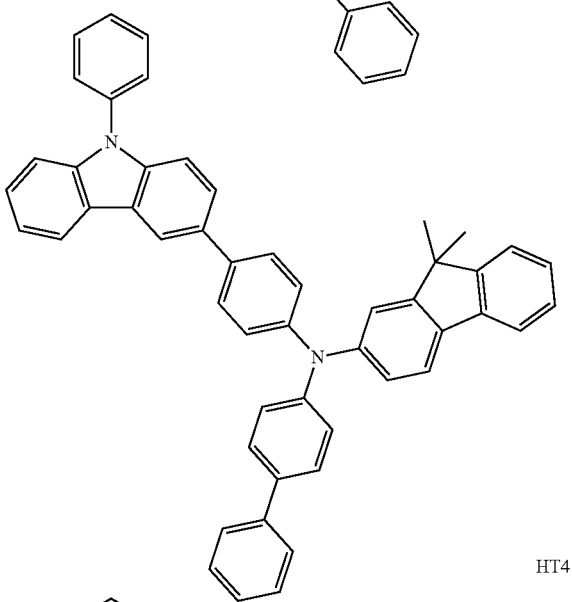

HT4

HT5
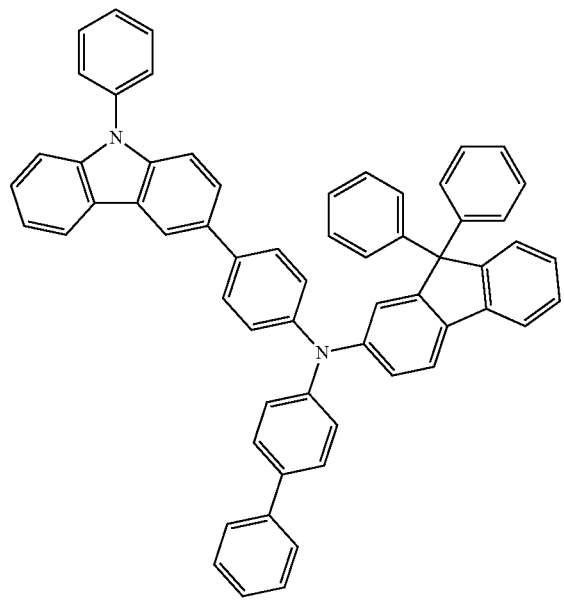
HT7
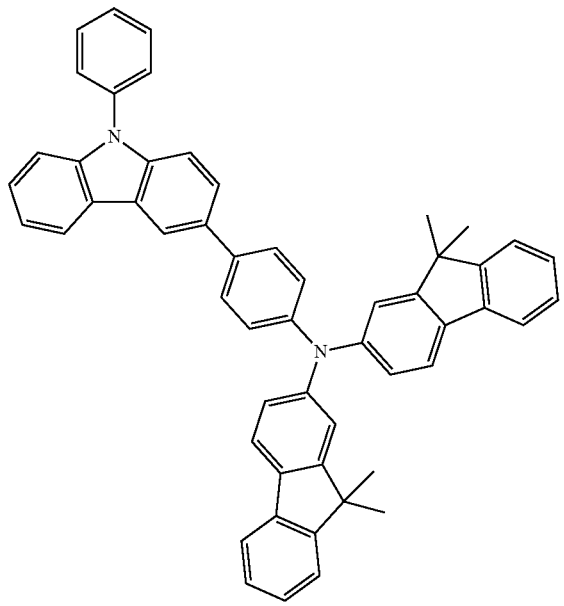
HT8
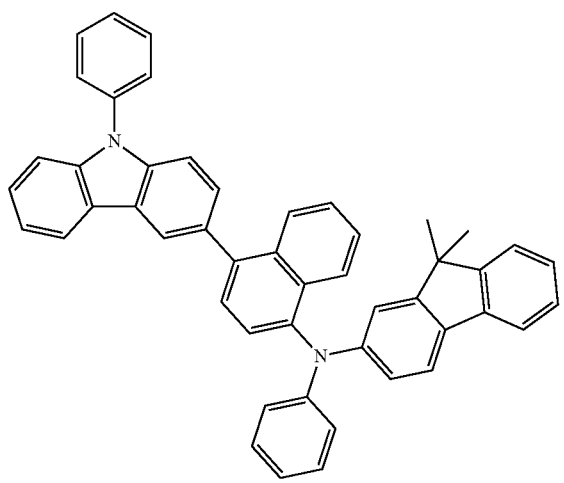
HT6
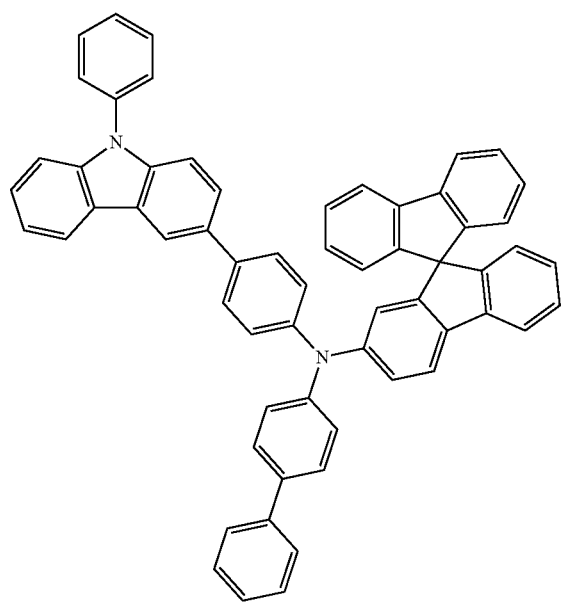
HT9

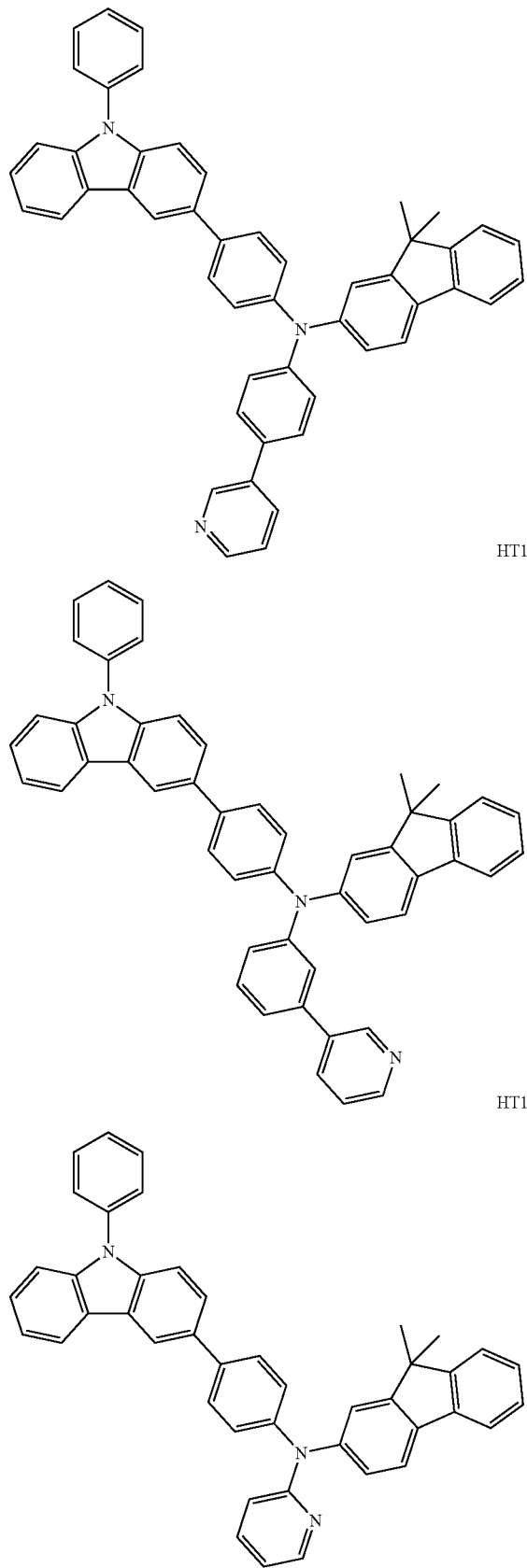
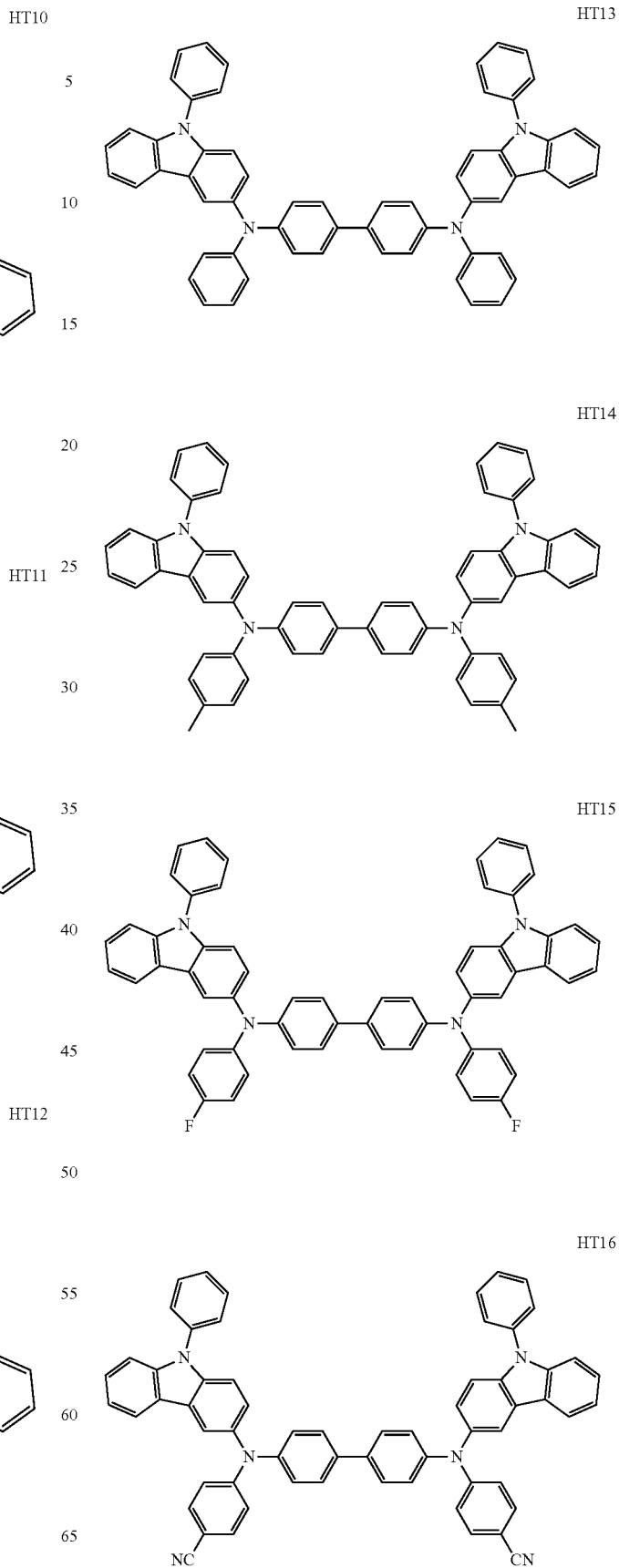

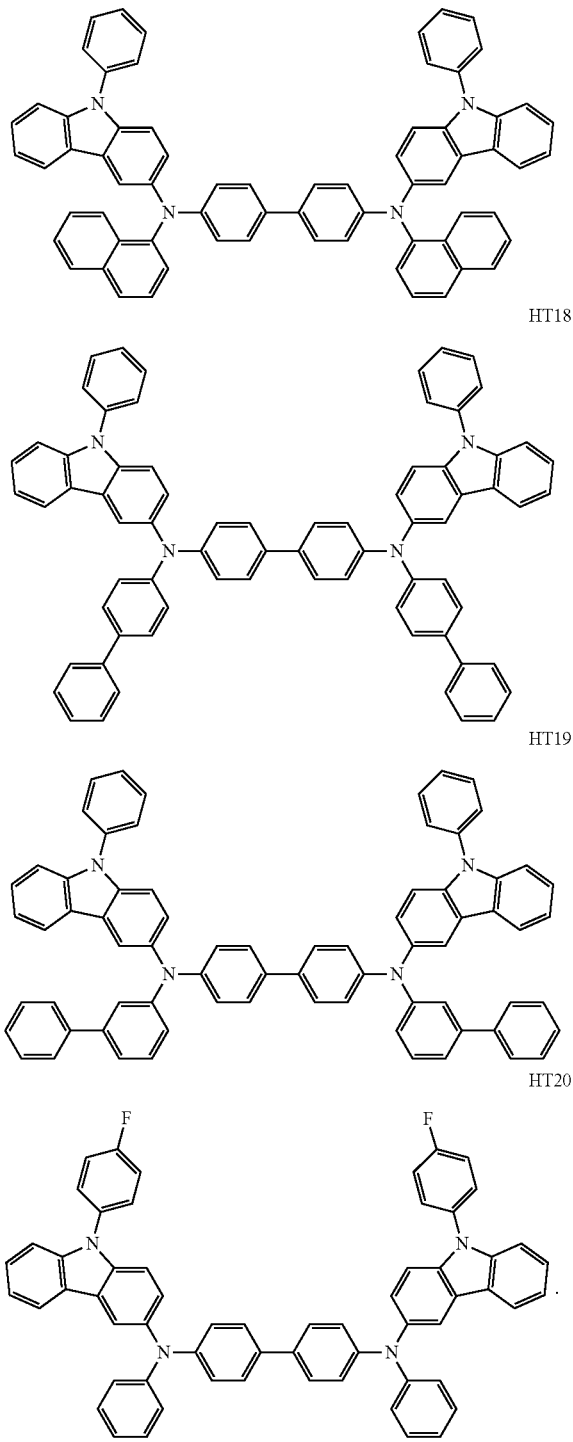

HT17

HT18

HT19

HT20

The thickness of the hole transport region may be in a range of about 100 Angstroms (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but embodiments are not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 or HT-D2, but embodiments are not limited thereto:

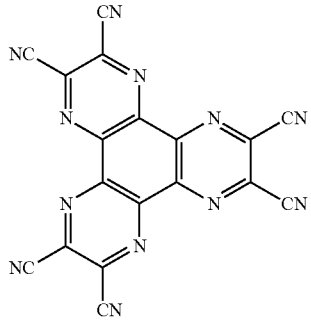

Compound HT-D1

F4-TCNQ

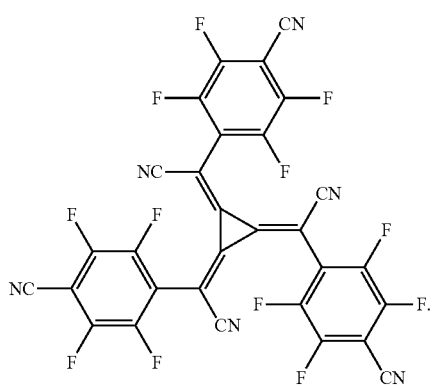

Compound HT-D2

The hole transport region may further include a buffer layer.

The buffer layer may compensate for an optical resonance distance according to a wavelength of light emitted from the emission layer to improve the efficiency of an organic light-emitting device.

An emission layer may be formed on the hole transport region by using various methods, such as vacuum-deposition, spin coating, casting, or an LB method. When the emission layer is formed by vacuum-deposition or spin coating, vacuum-deposition and coating conditions for the emission layer may be generally similar to the conditions for forming a hole injection layer, though the conditions may vary depending on the compound used.

The emission layer may include a host and a dopant.

The host may include at least one selected from CBP, CDBP, TCP, and mCP:

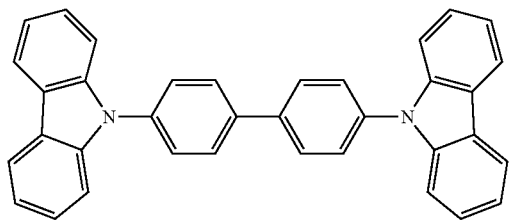

CBP

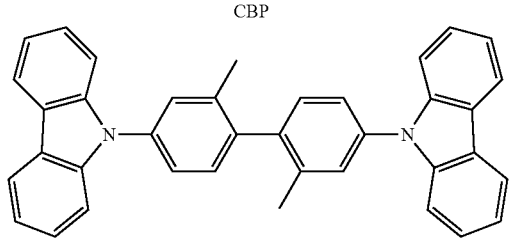

CDBP

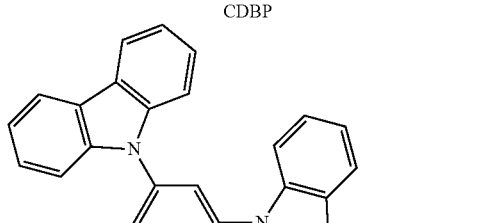

TCP

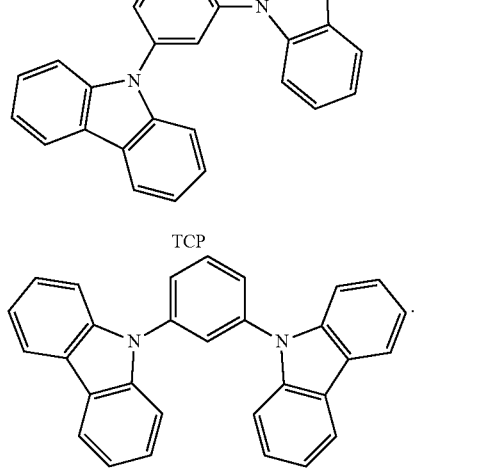

mCP

When the organic light-emitting device is a full color organic light-emitting device, the emission layer may be patterned into a red emission layer, a green emission layer, and a blue emission layer. Alternatively, the emission layer may have a structure in which the red emission layer, the green emission layer, and/or the blue emission layer are layered to emit white light or other various embodiments are possible.

The emission layer may include the organometallic compound represented by Formula 1 as a dopant.

When the emission layer includes the host and the dopant, the amount of the dopant may be selected from a range of about 0.01 part by weight to about 20 parts by weight based on about 100 parts by weight of the host, but embodiments are not limited thereto.

The thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be formed on the emission layer.

The electron transport region may include at least one selected from a hole blocking layer, an electron transport layer, and an electron injection layer, but embodiments not limited thereto.

For example, the electron transport region may have a structure of a hole blocking layer/an electron transport layer/an electron injection layer or an electron transport layer/an electron injection layer, but embodiments are not limited thereto. The electron transport layer may have a single layer structure or a multi-layer structure including two or more different materials.

The conditions for forming a hole blocking layer, an electron transport layer, and an electron injection layer may be inferred based on the conditions for forming the hole injection layer.

When the electron transport region includes an hole blocking layer, the hole blocking layer may, for example, include at least one of BCP and Bphen, but embodiments are not limited thereto:

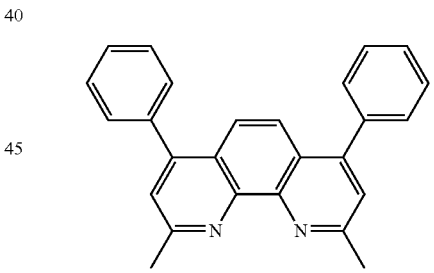

BCP

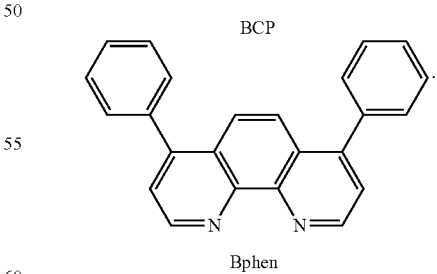

Bphen

The thickness of the hole blocking layer may be in a range of about 20 Å to about 1,000 Å, for example, about 30 Å to about 300 Å. When the thickness of the hole blocking layer is within this range, excellent hole blocking characteristics may be obtained without a substantial increase in driving voltage.

The electron transport layer may further include at least one selected from BCP, BPhen, Alq3, BAlq, TAZ, and NTAZ:
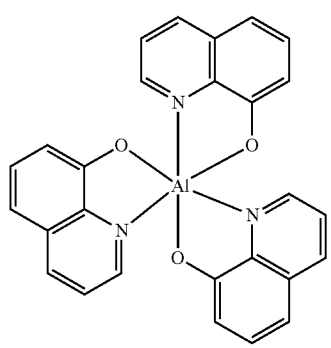
Alq3
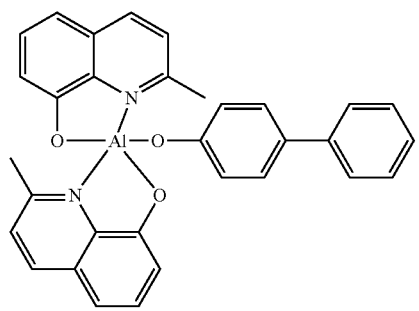
BAlq
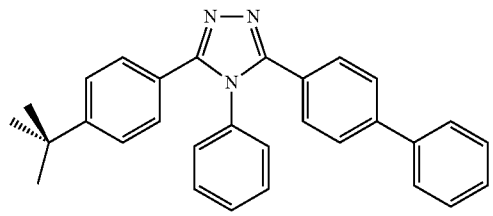
TAZ
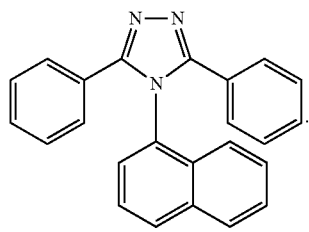
NTAZ
Alternatively, the electron transport layer may include at least one selected from Compounds ET1 to ET19, but embodiments are not limited thereto:
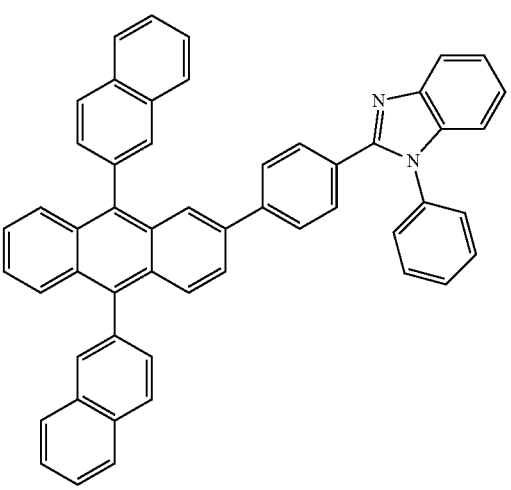
ET1
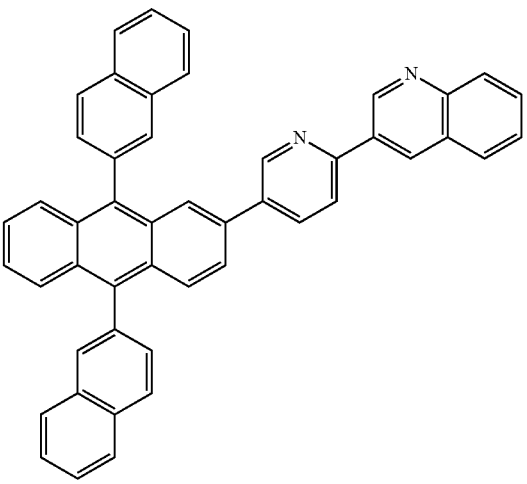
ET2
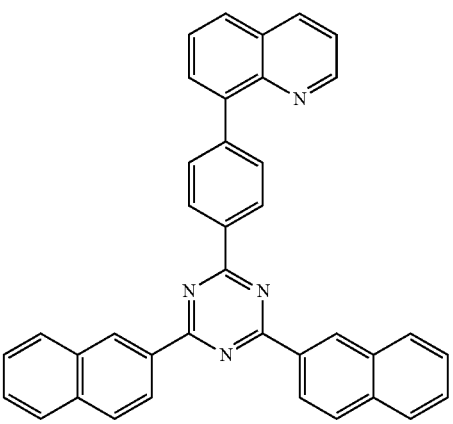
ET3

ET4
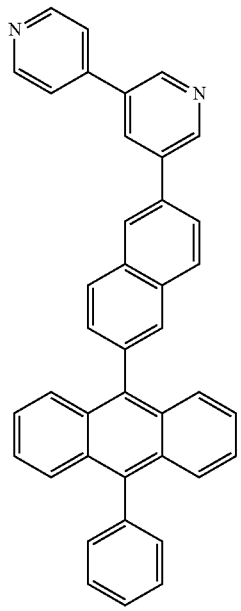
ET5
ET7
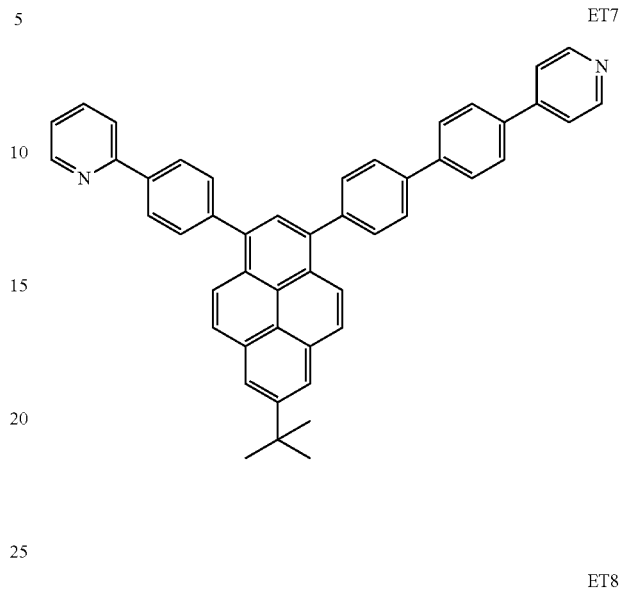
ET8
ET6
ET9
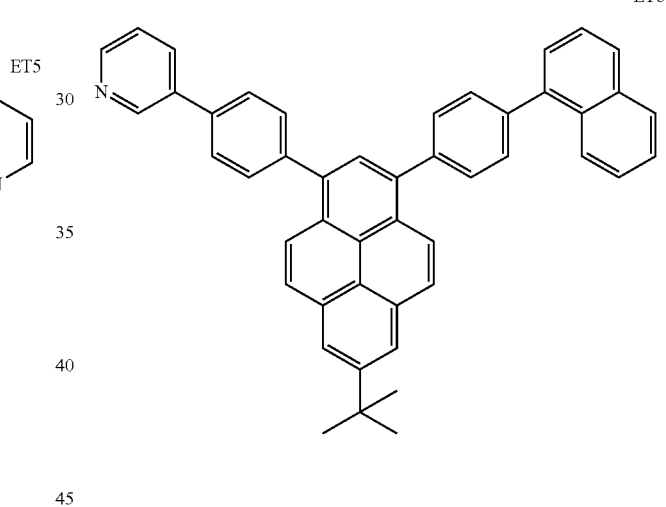
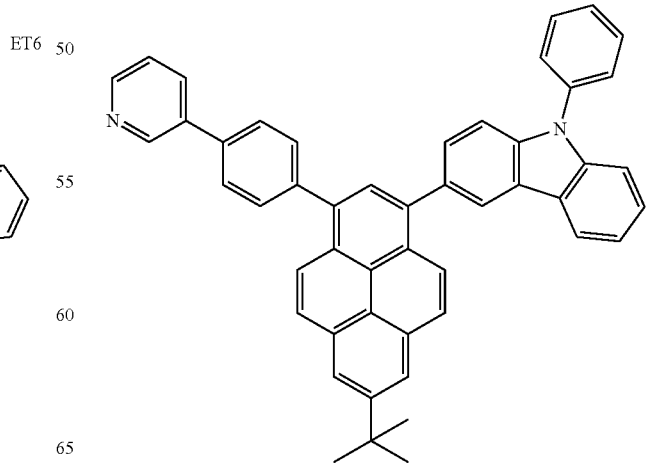

ET10
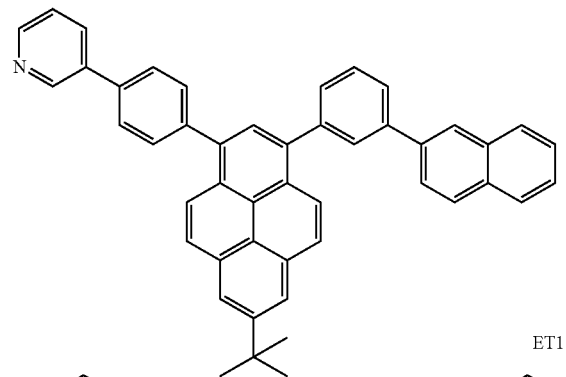
ET11
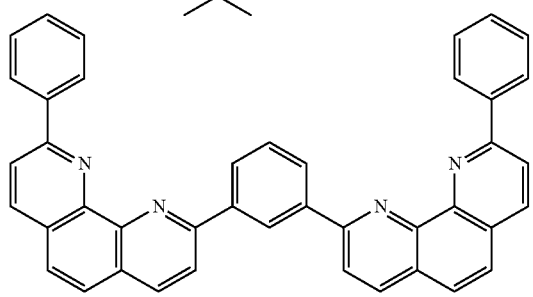
ET12
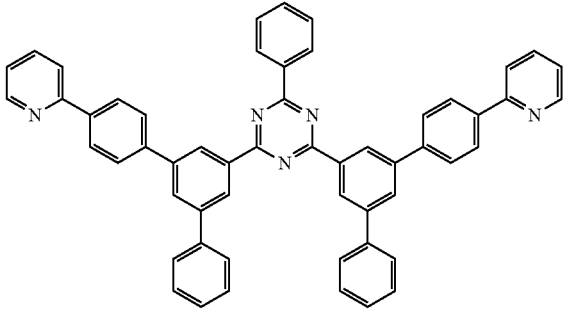
ET13
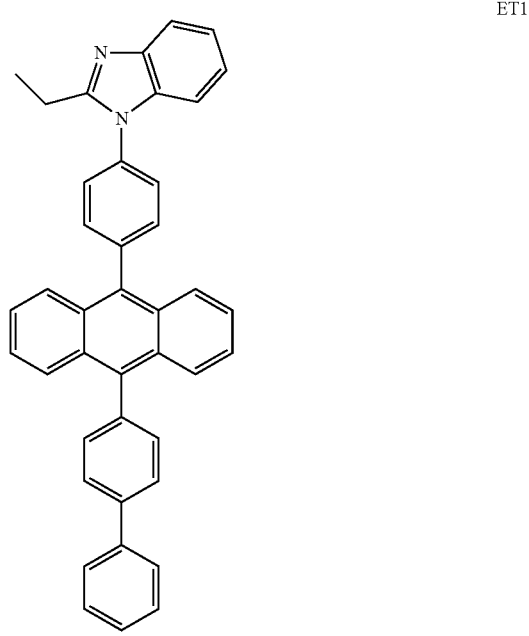
ET14
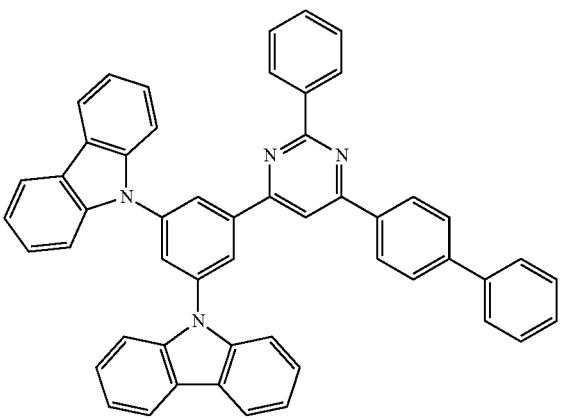
ET15
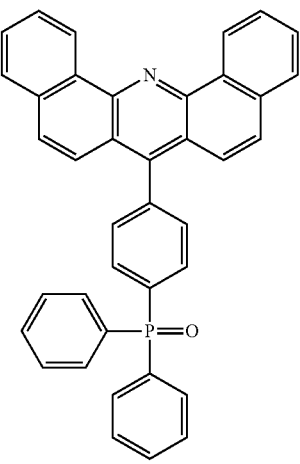
ET16
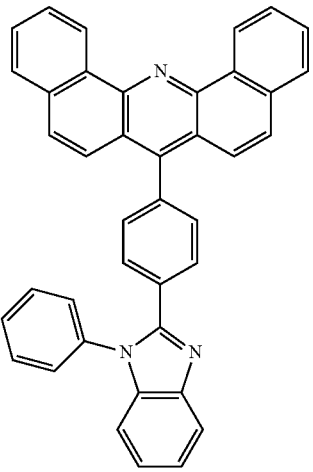

ET17

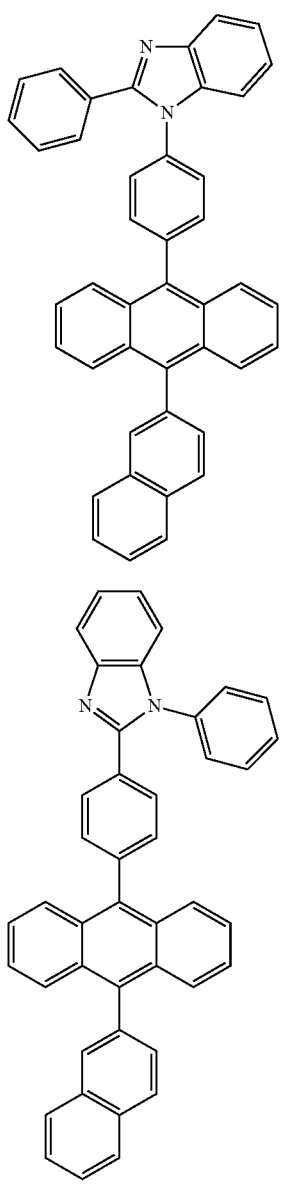

ET18

ET19

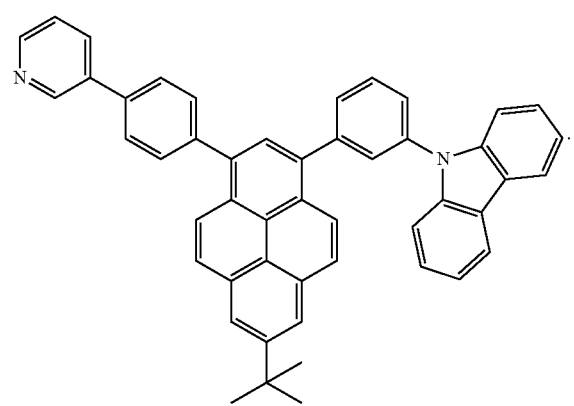

transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2:

ET-D1

ET-D2

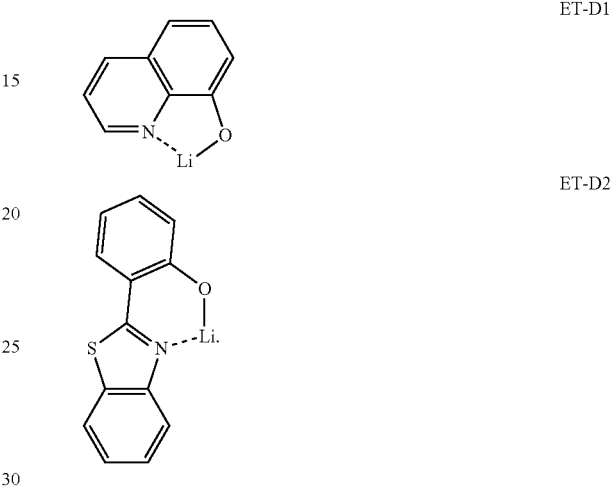

The electron transport region may include an electron injection layer that facilitates electron injection from the second electrode 19.

The electron injection layer may include at least one selected from LiF, NaCl, CsF, $Li_2O$, and BaO.

The thickness of the electron injection layer may be in a range of about 1 Å to about 100 Å, for example, about 3 Å to about 90 Å. When the thickness of the electron injection layer is within this range, excellent electron injection characteristics may be obtained without a substantial increase in driving voltage.

The second electrode 19 is disposed on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 are lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be used to form a transmissive second electrode 19 to manufacture a top emission light-emitting device, and such a variation may be possible.

Hereinbefore, the organic light-emitting device has been described with reference to FIG. 1, but embodiments are not limited thereto.

A $C_1$-$C_{10}$ alkyl group as used herein refers to a linear or branched aliphatic hydrocarbon monovalent group having 1 to 10 carbon atoms. Detailed examples thereof include a methyl group, an ethyl group, a propyl group, an iso-butyl group, a sec-butyl group, a tert-butyl group, a pentyl group, an iso-amyl group, and a hexyl group.

A $C_1$-$C_{10}$ linear alkyl group as used herein refers to a linear aliphatic hydrogen carbon monovalent group having 1 to 10 carbon atoms. A $C_1$-$C_{10}$ linear alkyl group is a $C_1$-$C_{10}$ alkyl group, excluding a branched alkyl group, such as The thickness of the electron transport layer may be in a range of about 100 Å to about 1,000 Å, for example, about 150 Å to about 500 Å. When the thickness of the electron iso-propyl group. Examples of the $C_1$-$C_{10}$ linear alkyl group include a n-propyl group and an n-butyl group.

A $C_1$-$C_{10}$ alkoxy group as used herein refers to a monovalent group represented by —$OA_{101}$ (wherein $A_{101}$ is a $C_1$-$C_{10}$ alkyl group). Detailed examples thereof are a methoxy group, an ethoxy group, and an isopropyloxy group.

A $C_2$-$C_{10}$ alkenyl group as used herein refers to a group formed by substituting at least one carbon double bond in the middle or at the terminal of the $C_2$-$C_{10}$ alkyl group. Detailed examples thereof are an ethenyl group, a propenyl group, and a butenyl group.

A $C_2$-$C_{10}$ alkynyl group as used herein refers to a group formed by substituting at least one carbon triple bond in the middle or at the terminal of the $C_2$-$C_{10}$ alkyl group. Detailed examples thereof are an ethenyl group and a propenyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one heteroatom selected from N, O, P, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one heteroatom selected from N, O, Si, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one heteroatom selected from N, O, P, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, and S as a ring-forming atom, and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group (e.g., a group having 8 to 60 carbon atoms) as used herein refers to a monovalent group that has two or more rings condensed to each other, has carbon atoms only as a ring-forming atom, and which is non-aromatic in the entire molecular structure. A detailed example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group (e.g., a group having 1 to 60 carbon atoms) as used herein refers to a monovalent group that has two or more rings condensed to each other, has heteroatoms as a ring-forming atom selected from N, O, P, and S in addition to C, and which is non-aromatic in the entire molecular structure. A detailed example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

In the present specification, at least one substituent of the substituted $C_1$-$C_{10}$ alkyl group, substituted $C_1$-$C_{10}$ linear alkyl group, substituted $C_2$-$C_{10}$ alkenyl group, substituted $C_2$-$C_{10}$ alkynyl group, and substituted $C_1$-$C_{10}$ alkoxy group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_2$-$C_{10}$ alkenyl group, a $C_2$-$C_{10}$ alkynyl group, and a $C_1$-$C_{10}$ alkoxy group; and a $C_1$-$C_{10}$ alkyl group, a $C_2$-$C_{10}$ alkenyl group, a $C_2$-$C_{10}$ alkynyl group, and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof.

Hereinafter, an organic light-emitting device according to an exemplary embodiment will be described in detail with reference to Synthesis Examples and Examples; however, the present inventive concept is not limited thereto. The wording "B was used instead of A" used in describing Synthesis Examples means that the amount of B used was identical to the amount of A used based on molar equivalence.

EXAMPLE

Synthesis Example 1: Synthesis of Compound 6

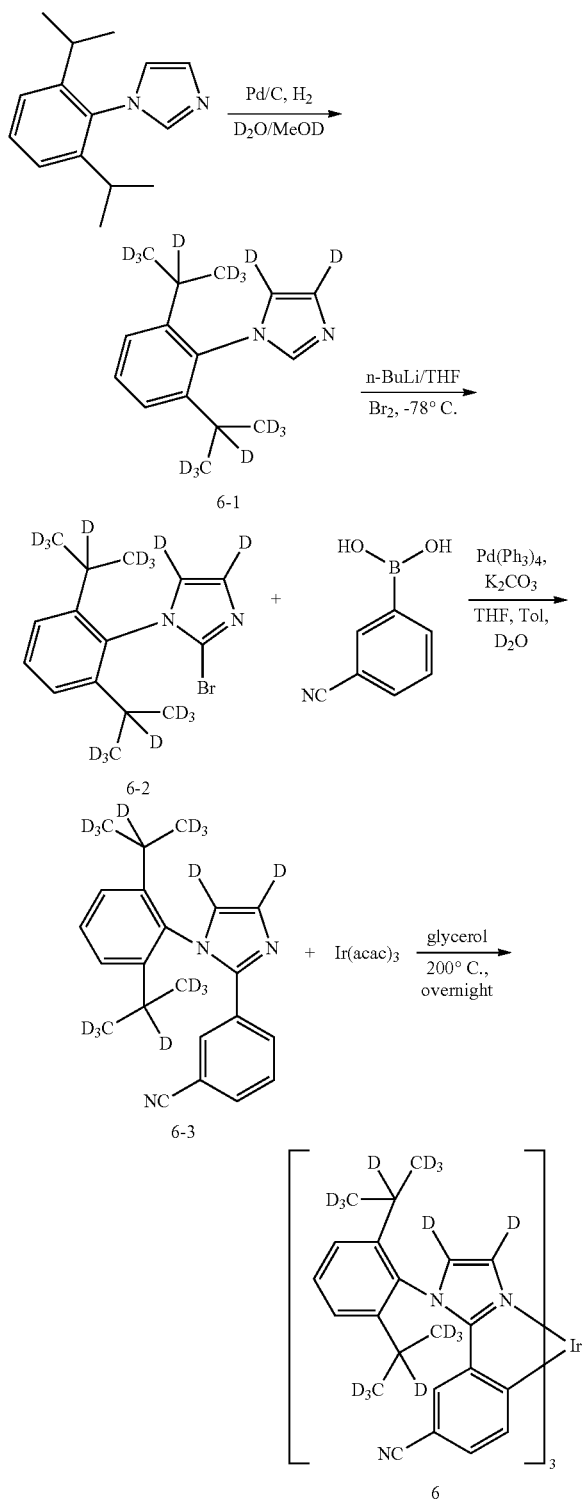

1) Synthesis of Intermediate 6-1

50 millimoles (mmol) (11.42 grams (g)) of 1-(2,6-diisopropylphenyl)-1H-imidazole and 2.5 mmol (5 percent by weight (wt %)) of Pd/C were mixed with 200 milliliters (ml) of $D_2O$ and 40 ml of MeOD. The mixture was stirred in a sealed tube at 180° C. under a hydrogen atmosphere for 24 hours. The resulting mixture was cooled, diluted in an ethyl acetate solution, and filtered. An organic layer was extracted with ethyl acetate. The obtained organic layer was washed with water three times and dried with magnesium sulfate ($MgSO_4$). The crude product was obtained therefrom by removing a solvent under reduced pressure. The crude product was purified by silica gel column chromatography (wherein, dichloromethane and hexane were used as an eluent), thereby obtaining 9.57 g of Intermediate 6-1 (yield: 90%).

MALDI-TOF (m/z): 239.33 $[M]^+$

2) Synthesis of Intermediate 6-2

9.57 g of Intermediate 6-1, 90 ml of tetrahydrofuran (THF), and 17.7 ml of n-BuLi (44 mmol, 2.5 M solution in n-hexane) were added to a reaction vessel under a nitrogen atmosphere, at −78° C. The mixture was stirred for about an hour. Thereafter, 40 mmol (6.39 g) of $Br_2$ was added thereto at −78° C. About 30 minutes after, a cooling bath was removed, and the resulting mixture was stirred at room temperature for about 6 hours. Once the reaction was complete, an organic layer was quenched with water and extracted with dichloromethane. The obtained organic layer was washed with water three times, and dried with $MgSO_4$. The crude product was obtained therefrom by removing a solvent under reduced pressure. The crude product was purified by silica gel column chromatography (wherein, dichloromethane and hexane were used as an eluent), thereby obtaining 9.64 g of Intermediate 6-2 (yield: 73%).

MALDI-TOF (m/z): 318.23 $[M]^+$

3) Synthesis of Intermediate 6-3

9.64 g (30 mmol) of Intermediate 6-2, 7.43 g (45 mmol) 3-cyano-4-fluorophenyl)boronic acid, 1.04 g (0.9 mmol) of tetrakis-(triphenylphosphine) palladium(0), 12.42 g (90 mmol) of potassium carbonate, 90 mL of toluene, and 60 mL of water were added to 90 mL of THF and the mixture was refluxed for 72 hours. The result was cooled, quenched with water, and the organic layer was extracted with ethyl acetate. The obtained organic layer was washed with water three times, and dried with $MgSO_4$. The crude product was obtained therefrom by removing a solvent under reduced pressure. The crude product was purified by silica gel column chromatography (wherein, dichloromethane and hexane were used as an eluent), thereby obtaining 8.64 g of Intermediate 6-3 (yield: 86%).

MALDI-TOF (m/z): 340.18 $[M]^+$

4) Synthesis of Compound 6

A mixture of 2.5 g (5 mmol) of $Ir(acac)_3$, 8.64 g (25 mmol) of Intermediate 6-3, and 150 mL of glycerol in a 500 mL reaction vessel was refluxed under a nitrogen atmosphere for 12 hours. Once the reaction was complete, the resulting mixture was cooled to room temperature. 300 mL of distilled water was added to the reaction vessel, thereby forming a solid. The formed solid was filtered and washed with 1 L of distilled water. The solid was dried, and was purified with silica gel column chromatography (wherein, dichloromethane and hexane were used as an eluent), thereby obtaining Compound 6 (yield: 24%).

MALDI-TOF (m/z): 1206.83 $[M]^+$

Synthesis Example 2: Synthesis of Compound 7

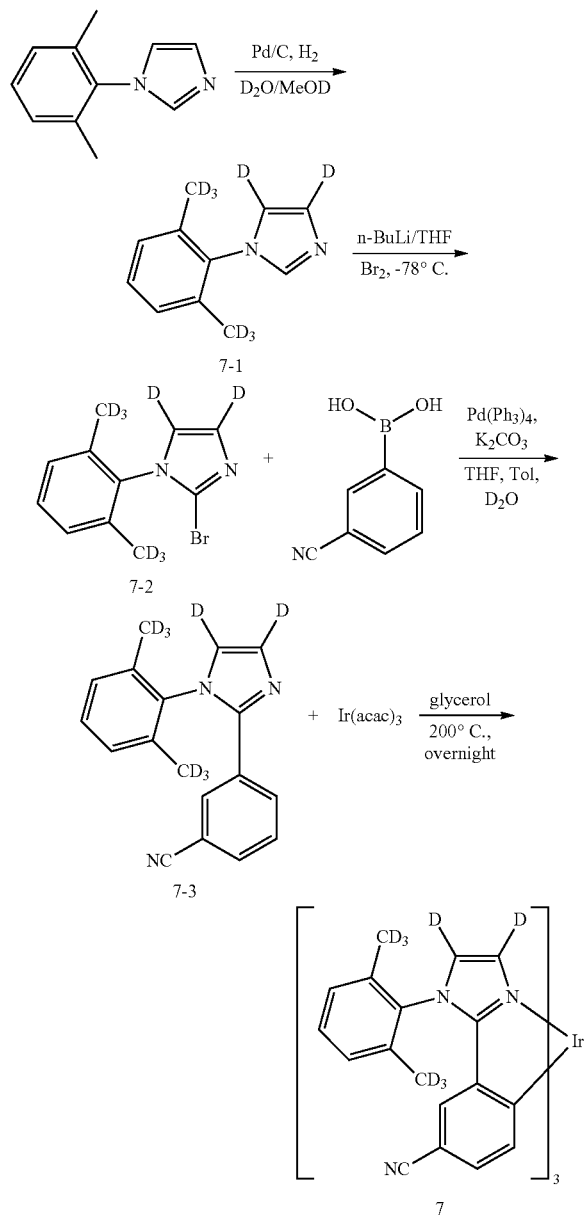

1) Synthesis of Intermediate 7-1

7.88 g of Intermediate 7-1 (yield: 88%) was synthesized in the same manner as Intermediate 6-1, except that 1-(2,6-dimethylphenyl)-1H-imidazole was used instead of 1-(2,6-diisopropylphenyl)-1H-imidazole.

MALDI-TOF (m/z): 179.10 [M]⁺

2) Synthesis of Intermediate 7-2

8.51 g of Intermediate 7-2 (yield: 75%) was synthesized in the same manner as Intermediate 6-2, except that Intermediate 7-1 was used instead of Intermediate 6-1.

MALDI-TOF (m/z): 257.99 [M]⁺

3) Synthesis of Intermediate 7-3

7.86 g of Intermediate 7-3 (yield: 85%) was synthesized in the same manner as Intermediate 6-3, except that Intermediate 7-2 was used instead of Intermediate 6-2.

MALDI-TOF (m/z): 280.20 [M]⁺

4) Synthesis of Compound 7

1.31 g of Compound 7 (yield: 18%) was synthesized in the same manner as Compound 6, except that Intermediate 7-3 was used instead of Intermediate 6-3.

MALDI-TOF (m/z): 1034.58 [M]⁺

Synthesis Example 3: Synthesis of Compound 16

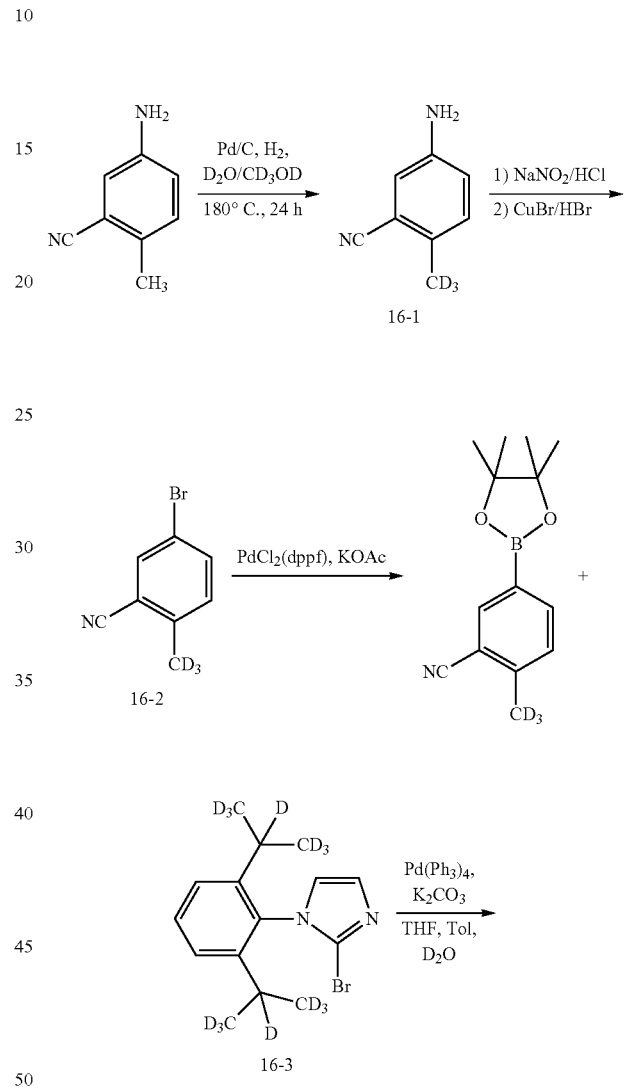

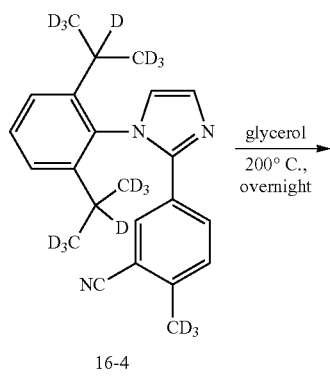

-continued

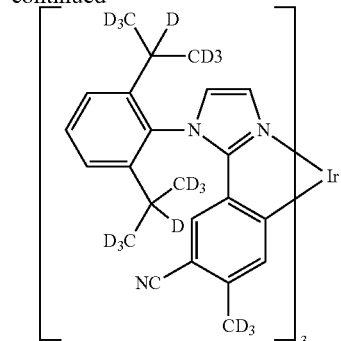

16

1) Synthesis of Intermediate 16-1

13.52 g of Intermediate 16-1 (yield: 90%) was synthesized in the same manner as Intermediate 6-1, except that 5-amino-2-methylbenzonitrile was used instead of 1-(2,6-diisopropylphenyl)-1H-imidazole.

MALDI-TOF (m/z): 135.21 $[M]^+$

2) Synthesis of Intermediate 16-2

13.52 g (100 mmol) of Intermediate 16-1 was added to 100 ml of acetonitrile, 6.90 g (100 mmol) of sodium nitrite dissolved in 50 ml of water at −25° C. was slowly added thereto, and subsequently, 34.5 ml (300 mmol) 48% HBr was slowly added thereto. The mixture was stirred for about an hour at −25° C. Thereafter, 150 mmol (21.55 g) of CuBr was added thereto. Then, a cooling bath was removed, and the resulting mixture was stirred at room temperature for about 20 hours. The reaction was quenched by adding water, and the pH thereof was adjusted to 10 by adding a saturated sodium carbonate solution. An organic layer was extracted with dichloromethane. The obtained organic layer was washed with water three times, and dried with MgSO$_4$. The crude product was obtained therefrom by removing a solvent under reduced pressure. The crude product was purified by silica gel column chromatography (wherein, dichloromethane and hexane were used as an eluent), thereby obtaining 9.95 g of Intermediate 16-2 (yield: 56%).

MALDI-TOF (m/z): 199.16 $[M]^+$

3) Synthesis of Intermediate 16-3

9.95 g (50 mmol) of Intermediate 16-3, 9.81 g (100 mmol) of potassium acetate, and 15.47 g (60 mmol) of 4,4,4',4',5,5,5',5'-octamethyl-2,2'-bi-1,3,2-dioxaborolane were added to 100 ml of N,N-dimethylformamide (DMF), and the mixture was stirred at room temperature. 2.56 g (3.5 mmol) of [1,1'-bis(diphenylphosphino)ferrocene]dichloro palladium (II) (PdCl$_2$(dppf)) was added thereto and the resulting mixture was refluxed at 80° C. for 12 hours. The obtained mixture was cooled, diluted by using ethyl acetate, and was filtered through celite. The obtained organic layer was washed with water three times, and dried by using MgSO$_4$. The crude product was obtained therefrom by removing a solvent under reduced pressure. The crude product was purified by silica gel column chromatography (wherein, dichloromethane and hexane were used as an eluent), thereby obtaining 8.72 g of Intermediate 16-3 (yield: 71%).

MALDI-TOF (m/z): 245.59 $[M]^+$

4) Synthesis of Intermediate 16-4

7.86 g of Intermediate 16-4 (yield: 85%) was synthesized in the same manner as Intermediate 6-3, except that Intermediate 16-2 was used instead of Intermediate 16-3.

MALDI-TOF (m/z): 260.38 $[M]^+$

5) Synthesis of Compound 16

2.76 g of Compound 16 (yield: 29%) was synthesized in the same manner as Compound 6, except that Intermediate 16-4 was used instead of Intermediate 6-3.

MALDI-TOF (m/z): 1261.63 $[M]^+$

Evaluation Example 1: Evaluation on HOMO, LUMO, and Triplet (T1) Energy Levels

HOMO, LUMO, and T1 energy levels of Compounds 6, 7, 16, and D to F were evaluated according to the method in Table 2. Results thereof are shown in Table 3.

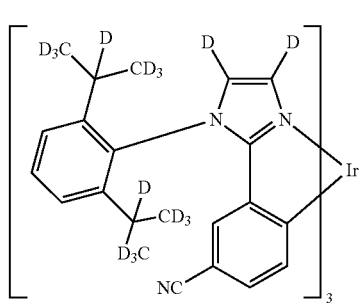

6

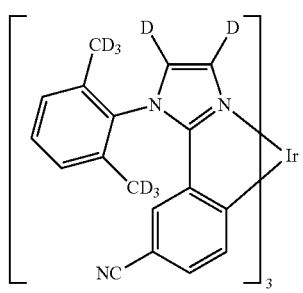

7

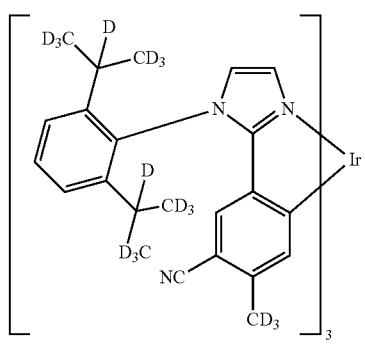

16

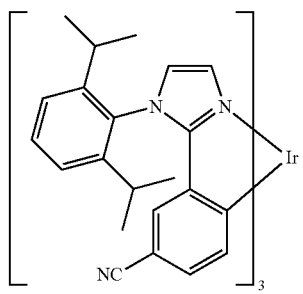

D

-continued

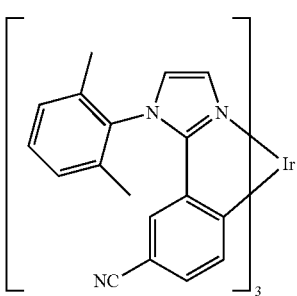

E

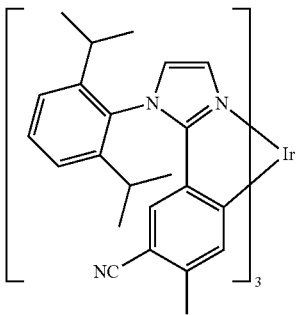

F

Evaluation Example 2: Thermal Characteristics Evaluation

Figure 2A:
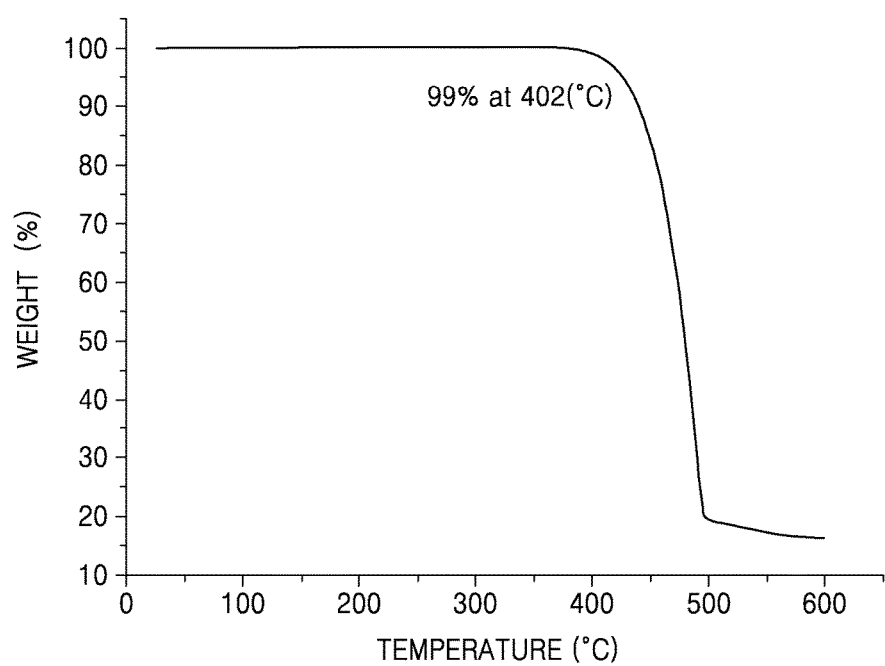
FIG. 2A is a graph of weight (%) versus temperature (degree Centigrade, ° C.), which shows a result of Thermo Gravimetric Analysis (TGA) on Compound 6 according to an embodiment.
Figure 2B:
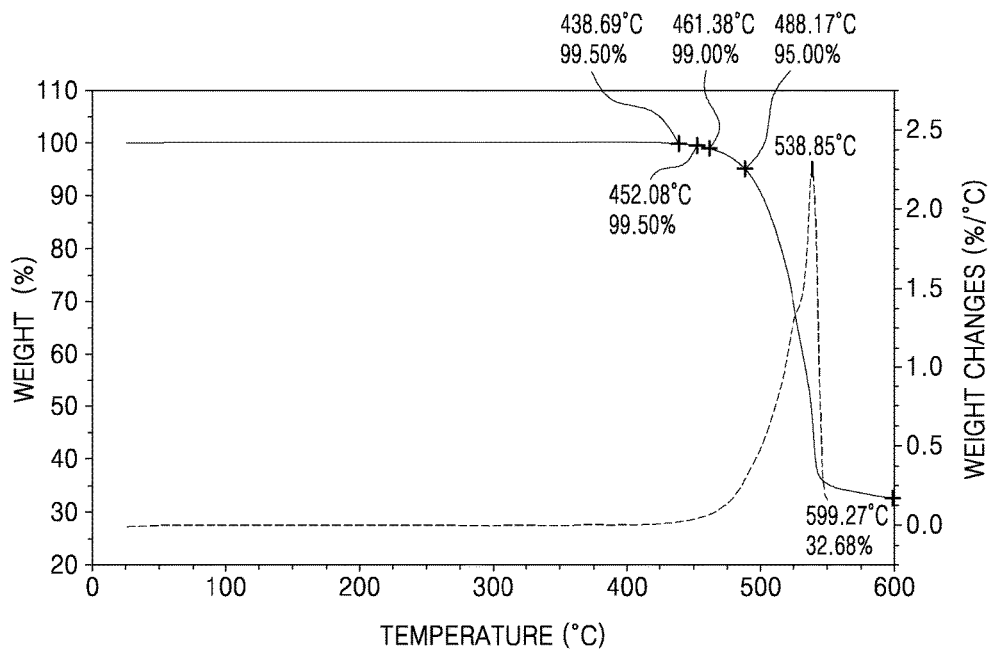
FIG. 2B is a graph of weight (%) and weight changes (percent per degree Centigrade, %/° C.) versus temperature (degree Centigrade, ° C.), which shows a result of TGA on Compound 7 according to an embodiment.

Thermal analysis (N$_2$ atmosphere, temperature range: room temperature to 600° C. (10° C./min), and Pan Type: Pt Pan in disposable Al Pan) was performed on Compounds 6, 7, 16, and D to F by using thermo gravimetric analysis (TGA). The results thereof are shown in Table 4. In addition, TGA results of Compounds 6 and 7 are shown in graphs in FIGS. 2A and 2B for illustrative purposes:

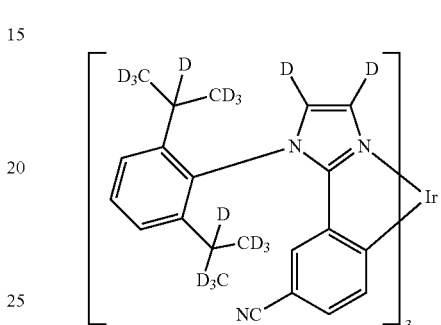

6

TABLE 2

| | |
|---|---|
| HOMO energy level evaluation method | A potential (Volts, V) - current (Amperes, A) graph of each compound was obtained by using cyclic voltammetry (CV) (electrolyte: 0.1M Bu$_4$NClO$_4$/ solvent: CH$_2$Cl$_2$/electrode: 3 electrode system (working electrode: GC, reference electrode: Ag/AgCl, auxiliary electrode: Pt)). Then, from reduction onset of the graph, a HOMO energy level of a compound was calculated. |
| LUMO energy level evaluation method | Each compound was diluted at a concentration of 1 × 10$^{-5}$M in CHCl$_3$, and a UV absorption spectrum thereof was measured at room temperature by using a Shimadzu UV-350 spectrometer. Then a LUMO energy level thereof was calculated by using an optical band gap (Eg) from an edge of the absorption spectrum. |
| T1 energy level evaluation method | A mixture (each compound was dissolved in an amount of 1 milligram (mg) in 3 cubic centimeters (cc) of toluene) of toluene and each compound was loaded into a quartz cell. Then, the resultant quartz cell was loaded into liquid nitrogen (77 Kelvin (K)), a photoluminescence spectrum thereof was measured by using a device for measuring photoluminescence, and the obtained spectrum was compared with a photoluminescence spectrum measured at room temperature, and peaks observed only at a low temperature were analyzed to calculate T1 energy levels. |

TABLE 3

| Compound No. | HOMO (eV) | LUMO (eV) | T1 (eV) |
|---:|---:|---:|---:|
| 6 | −5.36 | −2.41 | 2.69 |
| 7 | −5.28 | −2.53 | 2.69 |
| 16 | −5.27 | −2.49 | 2.72 |
| D | −5.42 | −2.75 | 2.68 |
| E | −5.35 | −2.60 | 2.68 |
| F | −5.21 | −2.27 | 2.71 |

From Table 3, it is found that Compounds 6, 7, and 16 have electric characteristics that are suitable as a material for forming an organic light-emitting device.

-continued

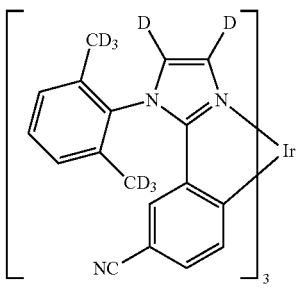

7

-continued

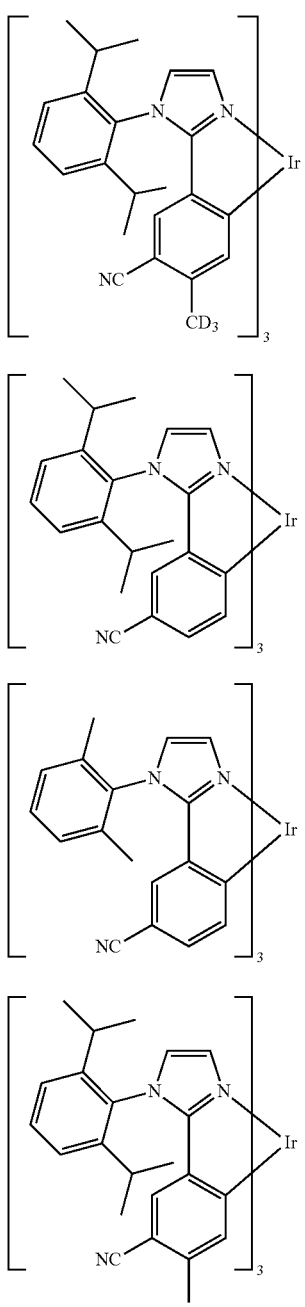

TABLE 4

| Compound No. | Td (1%, ° C.) |
|---|---|
| 6 | 402 |
| 7 | 461 |
| 16 | 383 |
| D | 398 |
| E | 445 |
| F | 368 |

Referring to Table 4, Compound 6 has higher Td than Compound D, Compound 7 has higher Td than Compound E, and Compound 16 has higher Td than Compound F. From Table 4, it was found that the organometallic compound represented by Formula 1 has excellent thermal stability due to substituting hydrogen atoms with deuterium atoms.

Evaluation Example 3: Emission Spectrum Evaluation

The Photoluminescence (PL) spectrum of Compounds 6, 7, 16, and A to F were measured to evaluate emission characteristics of each compound. Compound 6 was dissolved at a concentration of 10 millimolar (mM) in $CHCl_3$. Then an ISC PC1 spectrofluorometer, in which a Xenon lamp was mounted, was used to measure a PL spectrum of Compound 1 at room temperature. The same process was repeated for Compounds 7, 16, and D to F.

Figure 3A:
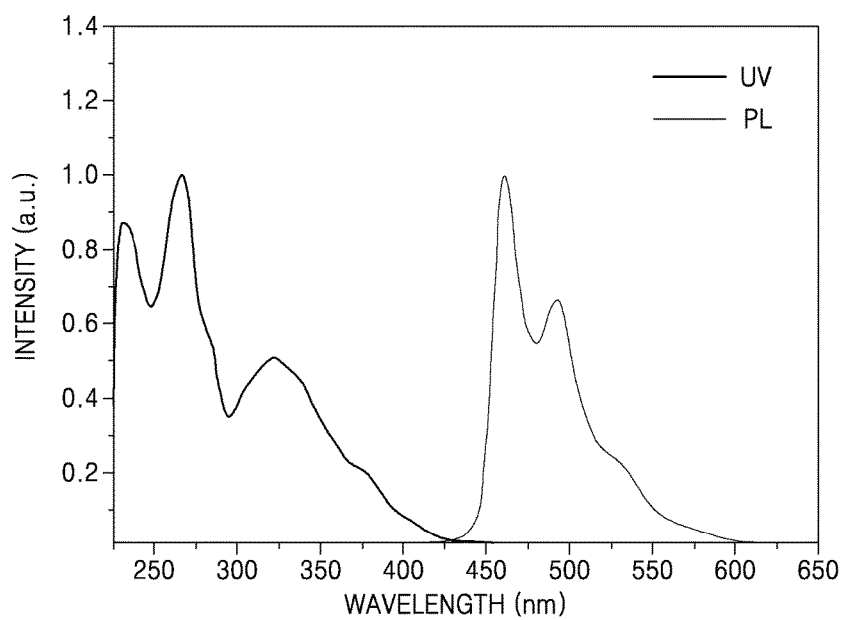
FIG. 3A is a graph of intensity (arbitrary units, a. u.) versus wavelength (nanometers, nm) showing a photoluminescence (PL) spectrum and an ultraviolet (UV) absorption spectrum of Compound 6 according to an embodiment.
Figure 3B:
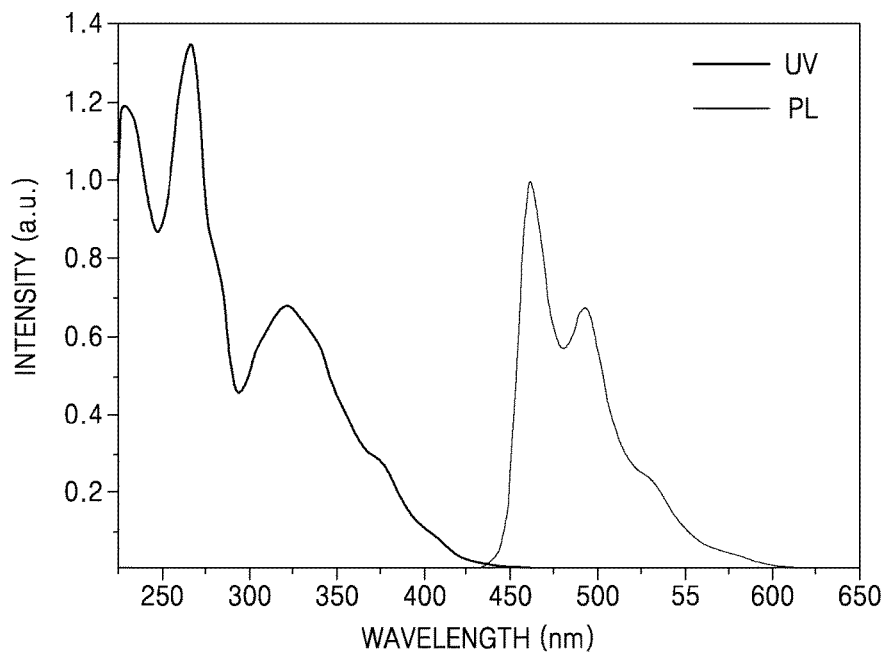
FIG. 3B is a graph of intensity (arbitrary units, a. u.) versus wavelength (nanometers, nm) showing a PL spectrum and a UV absorption spectrum of Compound 7 according to an embodiment.
Figure 4:
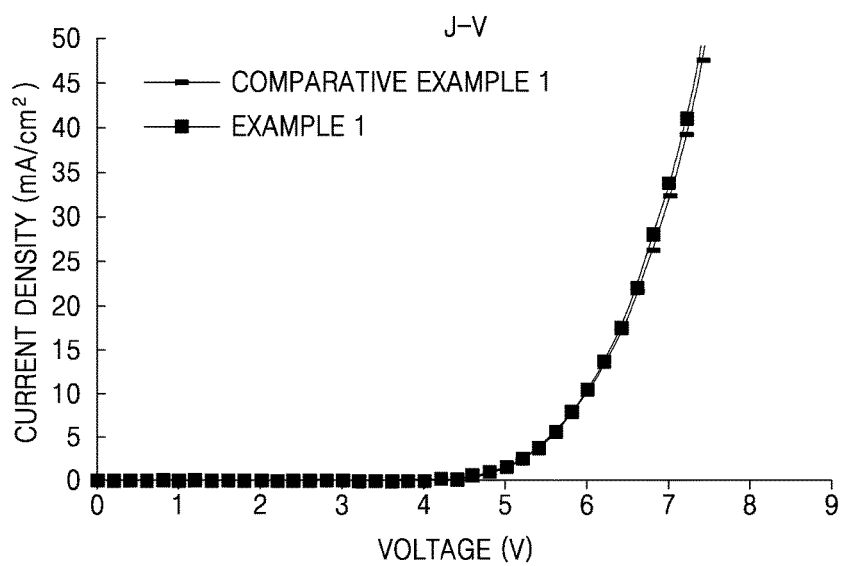
FIG. 4 is a graph of current density (milliamperes per square centimeter, $mA/cm^2$) illustrating current density changes according to voltages of organic light-emitting devices manufactured in Example 1 and Comparative Example 1.
Figure 5:
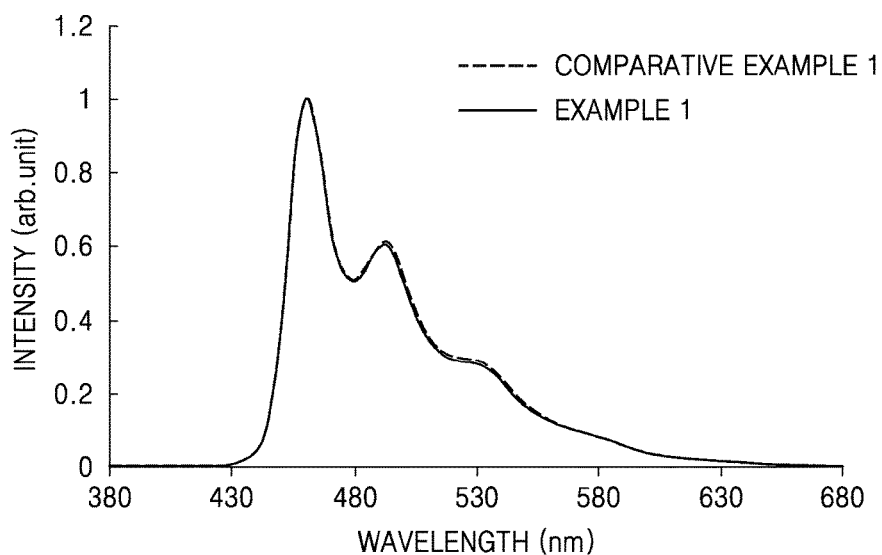
FIG. 5 is a graph of intensity (arbitrary units, a. u.) versus wavelength (nanometers, nm) showing electroluminescence (EL) spectrum of the organic light-emitting devices manufactured in Example 1 and Comparative Example 1.
Figure 6:
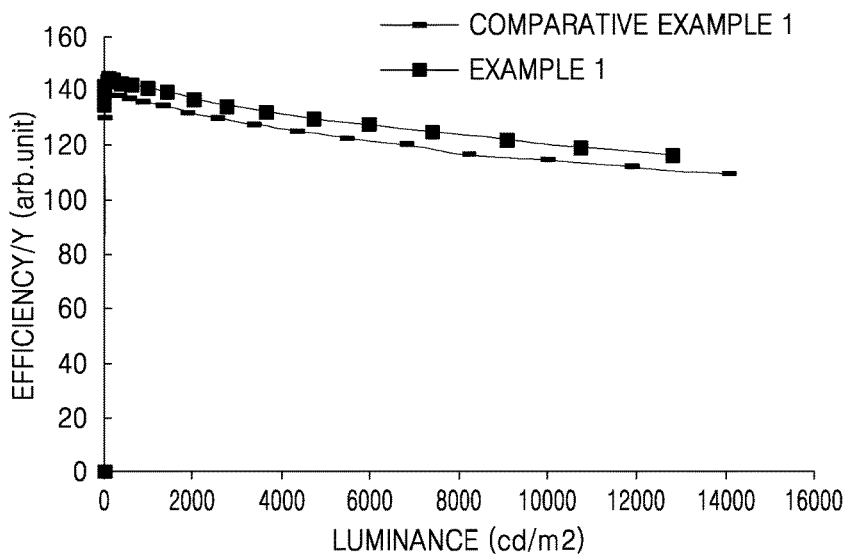
FIG. 6 is a graph of efficiency (arbitrary units, a. u.) versus luminance (candelas per square meter, cd/m$^2$) illustrating conversion efficiency changes according to luminance values of the organic light-emitting devices manufactured in Example 1 and Comparative Example 1.
Figure 7:
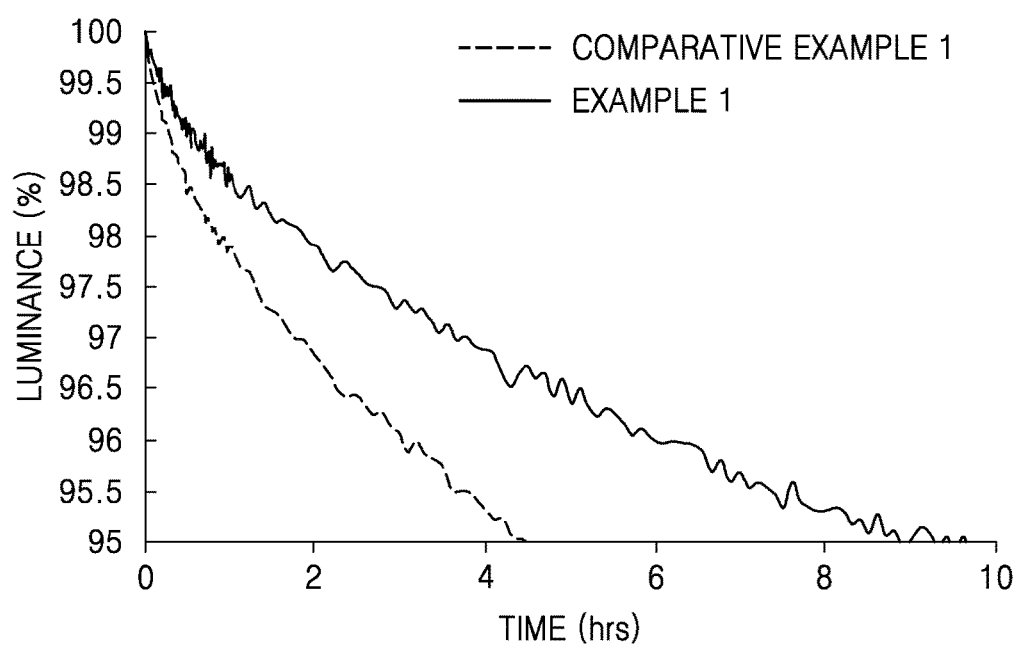
FIG. 7 is a graph of luminance (percent) versus time (hours, hrs) illustrating lifespan of the organic light-emitting devices manufactured in Example 1 and Comparative Example 1.

The maximum wavelength of PL spectra of Compounds 7, 16, and D to F are shown in Table 5. In addition, PL spectra of Compounds 6 and 7 are shown in FIGS. 3A and 3B, respectively.

TABLE 5

| Compound No. | $\lambda_{max}$ (nm) |
|---|---|
| 6 | 461 |
| 7 | 461 |
| 16 | 456 |
| D | 463 |
| E | 462 |
| F | 457 |

Referring to Table 5, it was found that compounds, in which a cyano group is positioned at a para position with respect to the Ir-carbon bond (that is, Compounds 6, 7, 16, and D to F), have a maximum emission wavelength of 465 nanometers (nm) or less. On the other hand, compounds, in which a cyano group is not positioned at a para position with respect to Ir-carbon bond (that is, Compounds A to C), have a maximum emission wavelength of greater than 465 nm. From the results above, it was found that in order to provide a deep blue emission color, it is desired that a cyano group is substituted at a para position with respect to the Ir-carbon binding site. From Table 5, it is found that the Compounds 6, 7, and 16 have excellent emission characteristics.

Example 1

As a first electrode (an anode), a glass substrate having an ITO electrode deposited thereon at a thickness of 1,500 Å was washed with distilled water in the presence of ultrasound waves. Once the washing with distilled water was complete, ultrasound wave washing was performed on the substrate by using a solvent such as isopropyl alcohol, acetone, or methanol. Then, the substrate was dried, transferred to a plasma washer, washed for 5 minutes using oxygen plasma, and mounted in a vacuum depositor.

Compound HT3 was vacuum-deposited on the ITO electrode of the glass substrate to form a first hole injection layer having a thickness of about 3,500 Å, Compound HT-D1 was vacuum-deposited on the first hole injection layer to form a second hole injection layer having a thickness of about 300 Å, and TAPC was vacuum-deposited on the second hole injection layer to form an electron blocking layer having a thickness of about 100 Å, thereby forming a hole transport region.

mCP (host) and Compound 1 (dopant, 7 wt %) were co-deposited on the hole transport region to form an emission layer having a thickness of about 300 Å.

Compound ET3 was vacuum-deposited on the emission layer to form an electron transport layer having a thickness of about 250 Å, ET-D1 (Liq) was vacuum-deposited on the electron transport layer to form an electron injection layer having a thickness of about 5 Å, and an Al second electrode (a cathode) was formed on the electron injection layer to have a thickness of about 1,000 Å, thereby completing the manufacture of an organic light-emitting device.

Example 2

An organic light-emitting device was manufactured in the same manner as in Example 1, except that Compound 7 was used instead of Compound 6 as a dopant in the formation of the emission layer.

Example 3

An organic light-emitting device was manufactured in the same manner as in Example 1, except that Compound 16 was used instead of Compound 6 as a dopant in the formation of the emission layer.

Comparative Example 1

An organic light-emitting device was manufactured in the same manner as in Example 1, except that Compound D was used instead of Compound 6 as a dopant in the formation of the emission layer.

Comparative Example 3

An organic light-emitting device was manufactured in the same manner as in Example 1, except that Compound E was used instead of Compound 6 as a dopant in the formation of the emission layer.

Comparative Example 2

An organic light-emitting device was manufactured in the same manner as in Example 1, except that Compound F was used instead of Compound 6 as a dopant in the formation of the emission layer.

Evaluation Example 4: Evaluation of Characteristics of Organic Light-Emitting Device The EL spectrum, current density change according to voltage, luminance change according to voltage, conversion efficiency, lifespan, and CIE color-coordinate of each organic light-emitting device manufactured in Example 1 and Comparative Example 1 were measured. A detailed measurement method is as described below, and the results thereof are shown in Table 6. In addition, the current density changes according to voltage, EL spectra, conversion efficiency changes according to luminance, and lifespan results of the organic light-emitting device manufactured in Example 1 and Comparative Example 1 are shown in FIGS. 4 to 7, respectively.

(1) Measurement of EL Spectra

EL spectra of the prepared organic light-emitting devices at a luminance of about 500 candelas per square meter ($cd/m^2$) were measured by using a luminance meter (Minolta Cs-1000A).

(2) Measurement of Current Density Changes According to Voltage

Current values of the prepared organic light-emitting devices were measured by measuring values of current in a unit device thereof using a current voltmeter (Keithley 2400) while increasing the applied voltage from about 0 Volts (V) to about 10 V. The result was obtained by dividing a current value by an area.

(3) Measurement of Luminance Changes According to Voltage

Luminance values of the prepared organic light-emitting devices were measured by using a luminance meter (Minolta Cs-1000A) while increasing the applied voltage from about 0 V to about 10 V.

(4) Measurement of Conversion Efficiencies

The luminance values measured from (3) and current density values measured from (2), and applied voltages were used in calculating current efficiencies (cd/A) under a condition of an identical current density (10 milliamperes per square centimeter ($mA/cm^2$)). Then, the current efficiencies were divided by a y value of the CIE color-coordinate measured in (6) in order to calculate conversion efficiencies.

(5) Measurement of Lifespan $T_{95}$, which indicates a period of time taken for the luminance to reach 95% with respect to 100% of the luminance measured in (3), and $T_{50}$, which indicates a period of time taken for the luminance to reach 50% with respect to 100% of the luminance measured in (3), were calculated.

(6) Measurement of CIE Color-Coordinate

Color-coordinates of the prepared organic light-emitting devices at a luminance of about 500 $cd/m^2$ were measured by using a luminance meter (Minolta Cs-1000A).

TABLE 6

| | Emission layer | | Current density | Luminance | Efficiency | Conversion | EL | T95 | T50 | Color-coordinate |
|---|---|---|---|---|---|---|---|---|---|---|
| | Host | Dopant | ($mA/cm^2$) | ($cd/m^2$) | (cd/A) | efficiency | (nm) | (Hour) | (Hour) | (x, y) |
| Example 1 | mCP | 6 | 10 | 500 | 37.21 | 143.20 | 460 | 8.88 | 360.00 | (0.17, 0.26) |
| Example 2 | mCP | 7 | 10 | 500 | 35.93 | 135.30 | 460 | 14.44 | 400.00 | (0.17, 0.27) |
| Example 3 | mCP | 16 | 10 | 500 | 31.54 | 150.20 | 456 | 4.66 | 160.00 | (0.16, 0.21) |
| Comparative Example 1 | mCP | D | 10 | 500 | 36.47 | 137.80 | 460 | 4.49 | 130.00 | (0.17, 0.26) |
| Comparative Example 2 | mCP | E | 10 | 500 | 35.57 | 125.50 | 460 | 2.42 | 110.00 | (0.17, 0.26) |
| Comparative Example 3 | mCP | F | 10 | 500 | 31.18 | 140.0 | 456 | 2.64 | 140.00 | (0.17, 0.23) |

Referring to Table 6, it is confirmed that the organic light-emitting devices prepared in Examples 1 to 3 have improved characteristics, compared to the organic light-emitting devices prepared in Comparative Examples 1 to 3.

As described above, according to the one or more of the above exemplary embodiments, the organometallic compound has excellent optical characteristics, electrical characteristics, and thermal stability. Accordingly, an organic light-emitting device using the organometallic compound may have improved efficiency, lifespan, and color purity characteristics.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:
1. An organometallic compound represented by Formula 1:

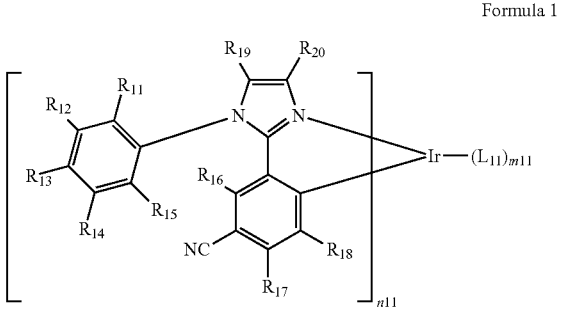

Formula 1 wherein in Formula 1,
$R_{11}$, $R_{12}$, and $R_{14}$ to $R_{18}$ are each independently selected from a hydrogen, a deuterium, —F, —Cl, —Br, —I, a hydroxy group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;
$R_{13}$ is selected from a hydrogen, a deuterium, —F, —Cl, —Br, —I, a hydroxy group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ linear alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;
$R_{19}$ and $R_{20}$ are each independently selected from a hydrogen, a deuterium, a $C_1$-$C_{10}$ alkyl group, and a $C_1$-$C_{10}$ alkyl group substituted with a deuterium;

$R_{11}$ and $R_{12}$, $R_{12}$ and $R_{13}$, $R_{13}$ and $R_{14}$, or $R_{14}$ and $R_{15}$ are optionally linked to each other to form a condensed ring;
at least one selected from $R_{11}$ to $R_{20}$ is a $C_1$-$C_{10}$ alkyl group substituted with a deuterium, provided that when $R_{13}$ is selected, $R_{13}$ is a $C_1$-$C_{10}$ linear alkyl group substituted with a deuterium;
n11 is selected from 1, 2, and 3;
$L_{11}$ is selected from a monodentate ligand and a bidentate ligand; and
m11 is selected from 0, 1, 2, 3, and 4.

2. The organometallic compound of claim 1, wherein $R_{11}$, $R_{12}$, and $R_{14}$ to $R_{18}$ are each independently selected from a hydrogen, a deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a substituted or unsubstituted $C_1$-$C_{10}$ alkyl group.

3. The organometallic compound of claim 1, wherein $R_{11}$, $R_{12}$, and $R_{14}$ to $R_{18}$ are each independently selected from
a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group; and
a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with a deuterium.

4. The organometallic compound of claim 1, wherein at least one of $R_{11}$ is $R_{15}$ are independently selected from
a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, and a tert-butyl group; and
a methyl group, an ethyl group, an n-propyl group, an iso-propyl group, an n-butyl group, a sec-butyl group, an iso-butyl group, and a tert-butyl group, each substituted with a deuterium.

5. The organometallic compound of claim 1, wherein $R_{13}$ is selected from a hydrogen, a deuterium, —F, —Cl, —Br, —I, a hydroxy group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, and a substituted or unsubstituted $C_1$-$C_{10}$ linear alkyl group.

6. The organometallic compound of claim 1, wherein $R_{13}$ is selected from a hydrogen, a deuterium, —F, —Cl, —Br, —I, a cyano group, a methyl group, an ethyl group, an n-propyl group, an n-butyl group, and an n-pentyl group; and
a methyl group, an ethyl group, an n-propyl group, an n-butyl group, and an n-pentyl group, each substituted with a deuterium.

7. The organometallic compound of claim 1, wherein
$R_{19}$ is a deuterium, and $R_{20}$ is a hydrogen;
$R_{19}$ is a hydrogen, and $R_{20}$ is a deuterium; or
$R_{19}$ and $R_{20}$ are both a deuterium.

8. The organometallic compound of claim 1, wherein at least one of $R_{11}$ and $R_{15}$ is a $C_1$-$C_{10}$ alkyl group substituted with a deuterium.

9. The organometallic compound of claim 1, wherein
the at least one selected from $R_{11}$ to $R_{20}$ is selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with a deuterium,
wherein selection of $R_{13}$ is subject to limitations of claim 1.

10. The organometallic compound of claim 1, wherein $L_{11}$ is a bidentate ligand.

11. The organometallic compound of claim 1, wherein $L_{11}$ is represented by one of Formulae 4-1 to 4-4:

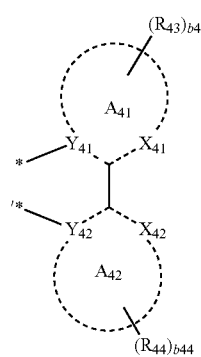

4-1

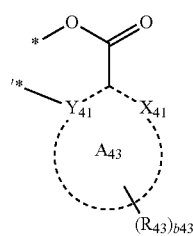

4-2

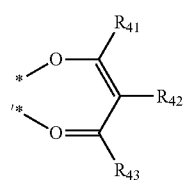

4-3

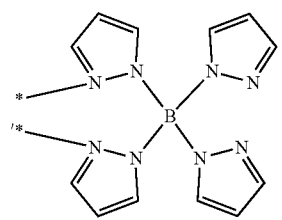

4-4 wherein in Formulae 4-1 to 4-4, $X_{41}$ is selected from $CR_{41}$ and N;
$X_{42}$ is selected from $CR_{42}$ and N;
$Y_{41}$ and $Y_{42}$ are each independently selected from C and N;
$A_{41}$ to $A_{43}$ are each independently selected from a $C_3$-$C_{10}$ cycloalkane, a $C_1$-$C_{10}$ heterocycloalkane, a $C_3$-$C_{10}$ cycloalkene, a $C_1$-$C_{10}$ heterocycloalkene, a $C_6$-$C_{10}$ arene, a $C_1$-$C_{10}$ heteroarene, a non-aromatic condensed polycycle, and a non-aromatic condensed heteropolycycle;
$R_{41}$ to $R_{44}$ are each independently selected from a hydrogen, a deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_{41}$)($Q_{42}$)($Q_{43}$);
b43 and b44 are each independently an integer selected from 1 to 5;
$Q_{41}$ to $Q_{43}$ are each independently selected from a hydrogen, a deuterium, —F, —Cl, —Br, —I, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and
* and *' each independently indicate a binding site to Ir in Formula 1.

12. The organometallic compound of claim 1, represented by Formula 1-1:

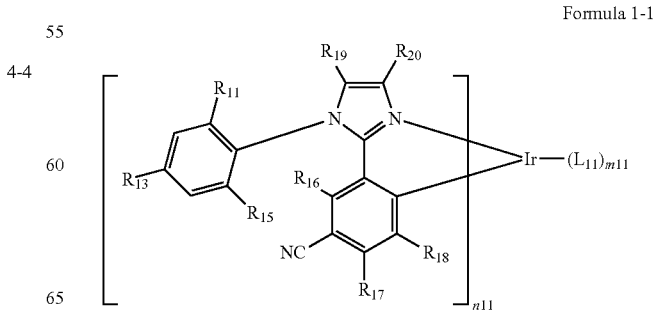

Formula 1-1 wherein in Formula 1-1, $R_{11}$, $R_{13}$, $R_{15}$ to $R_{20}$, $L_{11}$, n11, and m11 are the same as defined in Formula 1.

13. The organometallic compound of claim 1, represented by one of Formulae 1-21 and 1-22:

Formula 1-21

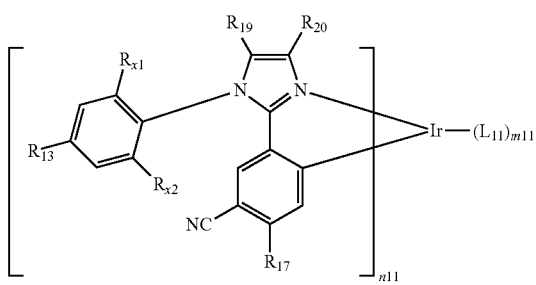

Formula 1-22

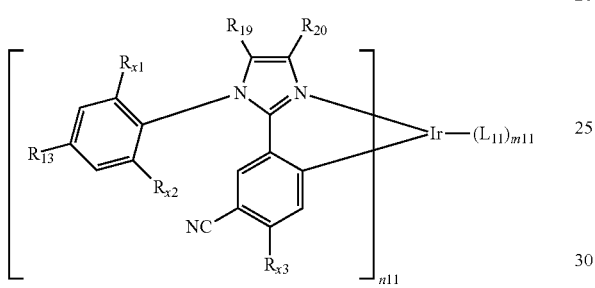

wherein in Formulae 1-21 and 1-22, $R_{13}$, $R_{17}$, $R_{19}$, $R_{20}$, $L_{11}$, n11, and m11 are the same as defined in Formula 1; and at least one of $R_{x1}$ to $R_{x3}$ is a $C_1$-$C_{10}$ alkyl group substituted with a deuterium.

14. The organometallic compound of claim 1, selected from Compounds 1 to 24:

1

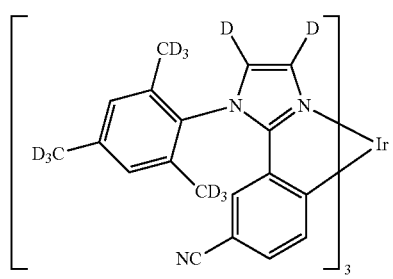

2

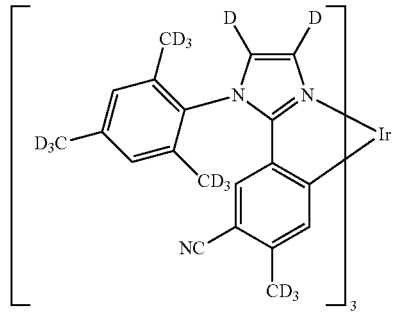

3

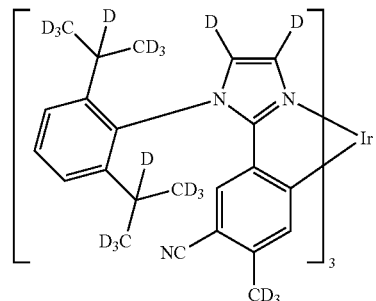

4

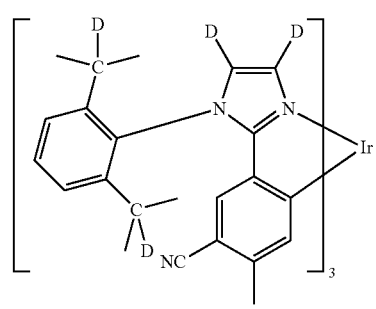

5

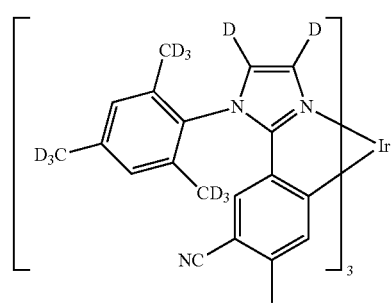

6

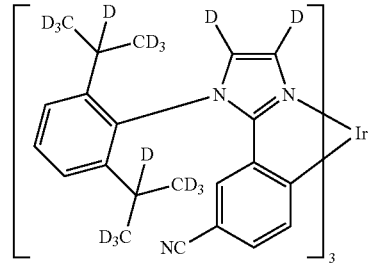

7

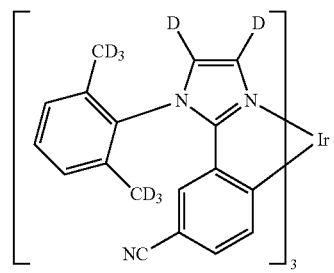

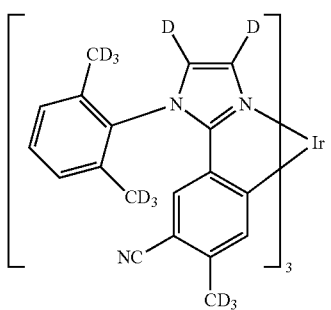
8
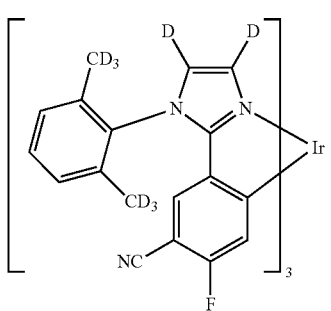
9
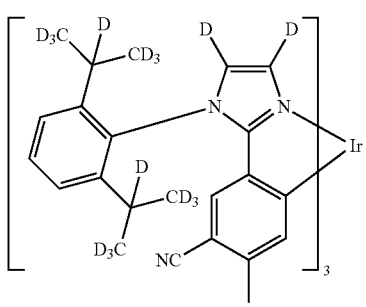
10
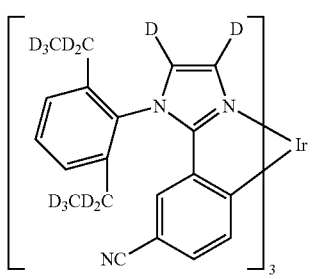
11
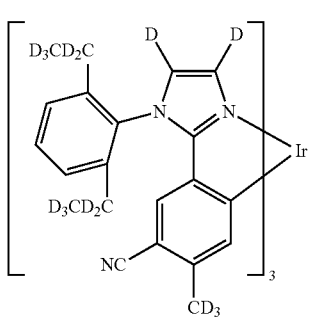
12
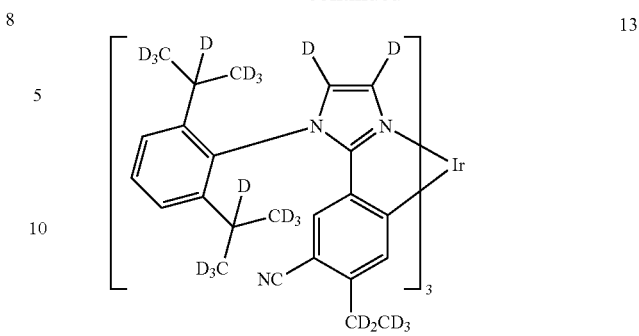
13
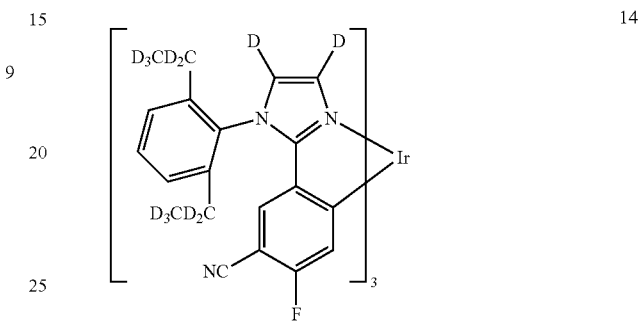
14
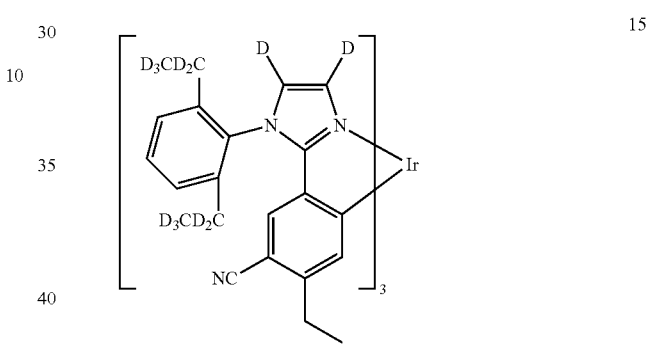
15
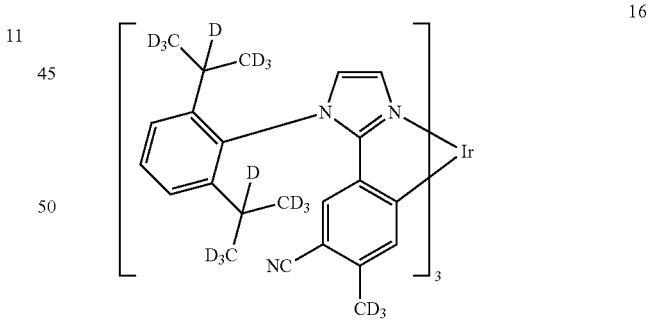
16
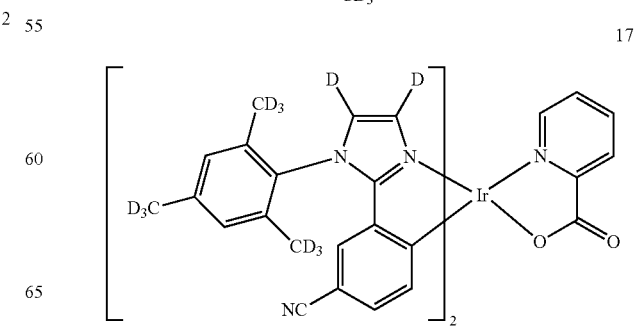
17

-continued

18
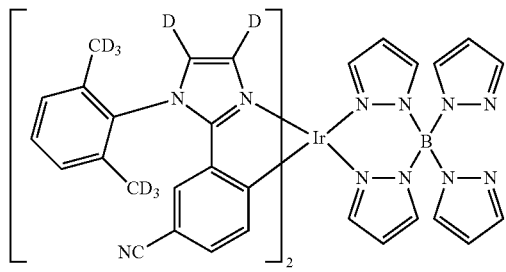

19
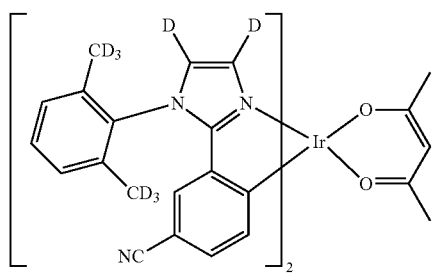

20
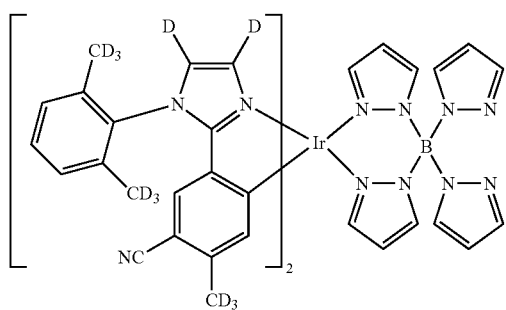

21
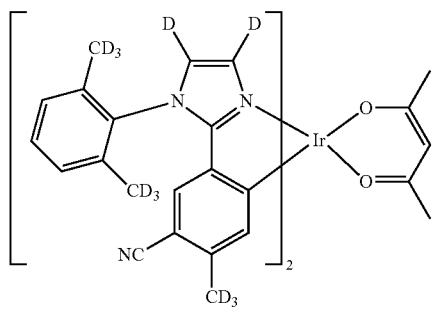

22
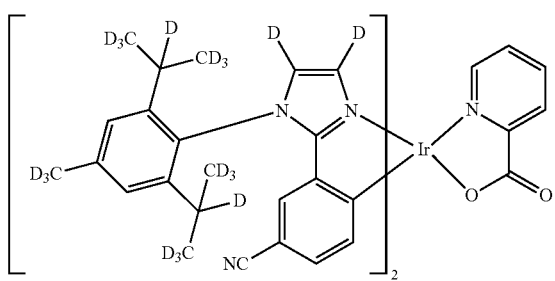

-continued

23
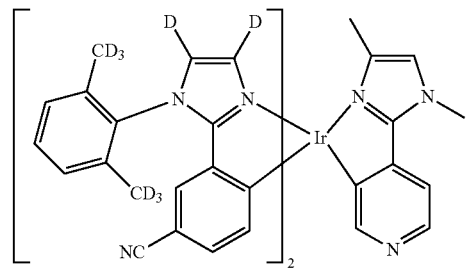

24
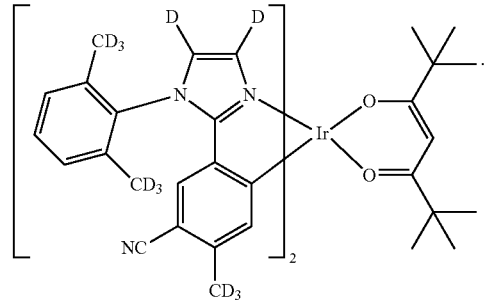

15. The organometallic compound of claim 1, wherein each of $R_{11}$, $R_{15}$, and $R_{17}$ is a $C_1$-$C_{10}$ alkyl group substituted with a deuterium.

16. A composition comprising an organometallic compound, comprising:
 a first organometallic compound represented by Formula 1 and
 a second organometallic compound represented by Formula 2:

Formula 1
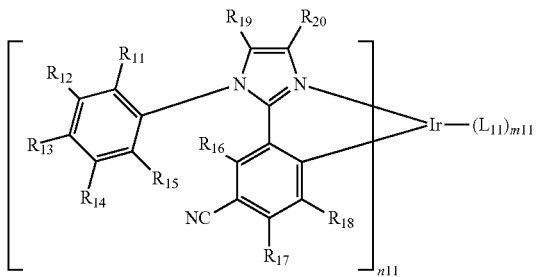

Formula 2
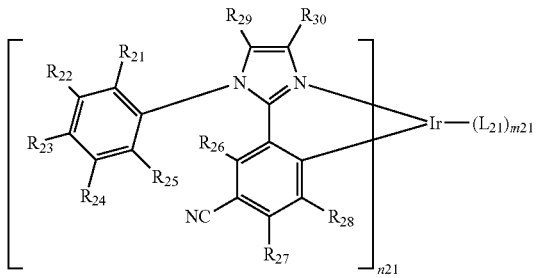

wherein in Formulae 1 and 2,
$R_{11}$, $R_{12}$, and $R_{14}$ to $R_{18}$ are each independently selected from a hydrogen, a deuterium, —F, —Cl, —Br, —I, a hydroxy group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{13}$ is selected from a hydrogen, a deuterium, —F, —Cl, —Br, —I, a hydroxy group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ linear alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{19}$ and $R_{20}$ are each independently selected from a hydrogen, a deuterium, a $C_1$-$C_{10}$ alkyl group, and a $C_1$-$C_{10}$ alkyl group substituted with a deuterium;

at least one of $R_{11}$ to $R_{20}$ comprises a deuterium;

$R_{21}$, $R_{22}$, and $R_{24}$ to $R_{28}$ are each independently selected from a hydrogen, —F, —Cl, —Br, —I, a hydroxy group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{23}$ is selected from a hydrogen, —F, —Cl, —Br, —I, a hydroxy group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ linear alkyl group, a substituted or unsubstituted $C_2$-$C_{10}$ alkenyl group, a substituted or unsubstituted $C_2$-$C_{10}$ alkynyl group, and a substituted or unsubstituted $C_1$-$C_{10}$ alkoxy group;

$R_{29}$ and $R_{30}$ are each independently selected from a hydrogen and a $C_1$-$C_{10}$ alkyl group;

$R_{21}$ to $R_{30}$ are each a substituent comprising no deuterium;

n11 and n21 are each independently selected from 1, 2, and 3;

$L_{11}$ and $L_{21}$ are each independently selected from a monodentate ligand and a bidentate ligand; and m11 and m21 are each independently selected from 0, 1, 2, 3, and 4.

17. The composition of claim 16, wherein the first organometallic compound has a deuteration degree of 50% or greater, as determined by Equation 2:

$$\text{Deuteration degree (\%)} = n_{D2}/(n_{H2}+n_{D2}) \times 100 \qquad \text{Equation 2}$$

wherein in Equation 2, $n_{H2}$ indicates the total number of hydrogens comprised in the at least one of $R_{11}$ to $R_{20}$ comprising deuterium of the first organometallic compound and the total number of hydrogens comprised in substituents of the second organometallic compound located at identical positions and corresponding to the at least one of $R_{11}$ to $R_{20}$ comprising deuterium of the first organometallic compound; and $n_{D2}$ indicates the total number of deuteriums comprised in the at least one of $R_{11}$ to $R_{20}$ of the first organometallic compound.

18. An organic light-emitting device comprising:
a first electrode;
a second electrode; and
an organic layer disposed between the first electrode and the second electrode, wherein the organic layer comprises an emission layer and the organometallic compound of claim 1.

19. The organic light-emitting device of claim 18,
wherein the emission layer comprises the organometallic compound;
wherein the emission layer further comprises a host; and
wherein the organometallic compound comprised in the emission layer is a dopant.

* * * * *